(12) United States Patent
Yang

(10) Patent No.: US 10,675,273 B2
(45) Date of Patent: Jun. 9, 2020

(54) BENZOTHIAZOLE AMPHIPHILES

(71) Applicant: The Regents of the University of California, Oakland, CA (US)

(72) Inventor: Jerry Yang, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/066,285

(22) PCT Filed: Jan. 4, 2017

(86) PCT No.: PCT/US2017/012139
§ 371 (c)(1),
(2) Date: Jun. 26, 2018

(87) PCT Pub. No.: WO2017/120198
PCT Pub. Date: Jul. 13, 2017

(65) Prior Publication Data
US 2019/0000811 A1 Jan. 3, 2019

Related U.S. Application Data

(60) Provisional application No. 62/274,907, filed on Jan. 5, 2016.

(51) Int. Cl.
| | |
|---|---|
| *A61K 31/426* | (2006.01) |
| *A61P 25/00* | (2006.01) |
| *A61K 47/10* | (2017.01) |
| *C07D 277/66* | (2006.01) |
| *A61P 35/00* | (2006.01) |

(52) U.S. Cl.
CPC ............ *A61K 31/426* (2013.01); *A61K 47/10* (2013.01); *A61P 25/00* (2018.01); *A61P 35/00* (2018.01); *C07D 277/66* (2013.01)

(58) Field of Classification Search
CPC ........ A61K 31/426; A61K 47/10; A61P 25/00
USPC ........................................................ 514/365
See application file for complete search history.

(56) References Cited

U.S. PATENT DOCUMENTS

| | | | |
|---|---|---|---|
| 2014/0080843 | A1 | 3/2014 | Huang et al. |
| 2015/0299191 | A1 | 10/2015 | Huang et al. |

FOREIGN PATENT DOCUMENTS

| | | | | |
|---|---|---|---|---|
| WO | WO-2014/134287 A1 | | 9/2014 | |
| WO | WO-2014134287 A1 | * | 9/2014 | ........... A61K 31/428 |

OTHER PUBLICATIONS

Cifelli, J.L. et al. (Jun. 15, 2016, e-published Apr. 12, 2016). "Benzothiazole Amphiphiles Ameliorate Amyloid β-Related Cell Toxicity and Oxidative Stress," *ACS Chem Neurosci* 7(6):682-688.
Inbar, P. et al. (Oct. 2006). "Oligo(ethylene glycol) derivatives of thioflavin T as inhibitors of protein-amyloid interactions," *ChemBioChem* 7(10):1563-1566.
International Search Report dated Mar. 30, 2017, for PCT Application No. PCT/US2017/012139, 2 pages.
Habib, L.K. et al. (Dec. 10, 2010, e-published Oct. 5, 2010). "Inhibitors of catalase-amyloid interactions protect cells from beta-amyloid-induced oxidative stress and toxicity," *J Biol Chem* 285(50):38933-38943.
Lee, N.J. et al. (Feb. 2016, e-published Dec. 8, 2015). "Hexa (ethylene glycol) derivative of benzothiazole aniline promotes dendritic spine formation through the RasGRF1-Ras dependent pathway," *Biochim Biophys Acta* 1862(2):284-295.
Megill, A. et al. (May 29, 2013). "A tetra(ethylene glycol) derivative of benzothiazole aniline enhances Ras-mediated spinogenesis," *J Neurosci* 33(22):9306-9318.
Prangkio, P. et al. (Dec. 2011, e-published Aug. 26, 2011). "Self-assembled, cation-selective ion channels from an oligo(ethylene glycol) derivative of benzothiazole aniline," *Biochim Biophys Acta* 1808(12):2877-2885.
Prangkio, P. et al. (2012, e-published Oct. 15, 2012). "Multivariate analyses of amyloid-beta oligomer populations indicate a connection between pore formation and cytotoxicity," *PLoS One* 7(10):e47261.
Song, J.M. et al. (Feb. 2014, e-published Dec. 6, 2013). "A tetra(ethylene glycol) derivative of benzothiazole aniline ameliorates dendritic spine density and cognitive function in a mouse model of Alzheimer's disease," *Exp Neurol* 252:105-113.
Written Opinion dated Mar. 30, 2017, for PCT Application No. PCT/US2017/012139, 2 pages.
Yang, J. et al. (Jul. 26, 2002). "Catalytic oxidations of steroid substrates by artificial cytochrome p-450 enzymes," *J Org Chem* 67(15):5057-5067.
Zhao, X. et al. (Oct. 20, 2010). "Amyloid-β peptide is a substrate of the human 20S proteasome," *ACS Chem Neurosci* 1(10):655-660.
Cifelli, J.L. et al. (Jun. 3, 2016, e-published Mar. 28, 2016). "Benzothiazole Amphiphiles Promote the Formation of Dendritic Spines in Primary Hippocampal Neurons," *J Biol Chem* 291(23):11981-11992.
Supplementary European Search Report dated Jul. 19, 2019, for EP Patent Application No. 17736233.2, 13 pages.

* cited by examiner

*Primary Examiner* — Yong L Chu
(74) *Attorney, Agent, or Firm* — Mintz, Levin, Cohn, Ferris, Glovsky and Popeo, P.C.; Doris Lee

(57) ABSTRACT

Disclosed herein, inter alia, are compounds and methods for increasing spine density in a neuron, and for treatment of neuronal diseases and cancer.

12 Claims, 18 Drawing Sheets

| Compound | log P[a] | SASA (Å²)[b] | $\lambda_{water}$ (nm) | $\lambda_{oct.}$ (nm) | $\lambda_{lip.}$ (nm) | Relative $\Delta\lambda_{max}$ (lip.-water) | IC$_{50}$ (μM) |
|---|---|---|---|---|---|---|---|
| BTA-EG$_6$ | 3.14 | 998 | 429.5 | 416.5 | 423 | 50% | 90 ± 3 |
| 1 | 2.64 | 967.6 | 433 | 417.5 | 428.5 | 29% | 171 ± 5 |
| 2 | 3.24 | 983 | 431.5 | 415.5 | 426.5 | 31% | 150 ± 4 |
| 3 | 3.26 | 976.6 | 410 | 394 | 404.5 | 34% | 140 ± 5 |

Higher expression of protein target in brain cancer (gliablastoma) patients (N = 521) correlates with overall lower survival BTA-EG$_4$ analogs exhibit anti-migration activity in human gliablastoma cells in a Boyden-chamber cell migration assay

BENZOTHIAZOLE AMPHIPHILES

CROSS-REFERENCES TO RELATED APPLICATIONS

This application is the national stage filing under USC 371 of international application PCT/US2017/012139, filed Jan. 4, 2017, which claims the benefit of U.S. Provisional Application No. 62/274,907, filed Jan. 5, 2016, which are incorporated herein by reference in their entirety and for all purposes,

STATEMENT AS TO RIGHTS TO INVENTIONS MADE UNDER FEDERALLY SPONSORED RESEARCH AND DEVELOPMENT

This invention was made with government support under Grant No. AG005131 and GM074240 awarded by the National Institutes of Health. The government has certain rights in the invention.

BACKGROUND

Dendritic complexity, synaptogenesis, and overall proper development and function of neurons are regulated by growth factors such as brain derived neurotrophic factor (BDNF). Estrogen (specifically, estradiol) is an example of a small molecule that is known to promote dendritic spine density in rodents and has been shown to improve cognition in humans. Unfortunately, the well-documented, harmful, long-term effects (e.g., increased risk of cancer, stroke and heart disease) of estrogen therapy preclude its general use for treating neuronal diseases. Disclosed herein, inter alia, are solutions to these and other problems in the art.

BRIEF SUMMARY OF THE INVENTION

In an aspect is provided a compound having the formula (I):

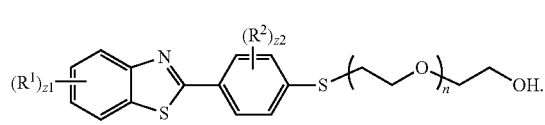

$R^1$ is independently halogen, $-CX^1_3$, $-CHX^1_2$, $-CH_2X^1$, $-OCX^1_3$, $-OCHX^1_2$, $-OCH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, $-CX^2_3$, $-CHX^2_2$, $-CH_2X^2$, $-OCX^2_3$, $-OCHX^2_2$, $-OCH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols $X^1$ and $X^2$ are independently halogen. The symbols z1 and z2 are independently an integer from 0 to 4. The symbol n is an integer from 1 to 20.

In another aspect is a complex (e.g., an in vitro complex) including a fascin protein non-covalently bound to a compound having the formula (II):

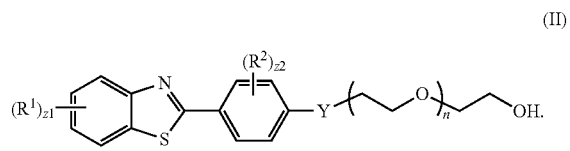

The symbol Y is $-NR^3-$ or $-S-$. $R^1$ is independently halogen, $-CX^1_3$, $-CHX^1_2$, $-CH_2X^1$, $-OCX^1_3$, $-OCHX^1_2$, $-OCH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, $-CX^2_3$, $-CHX^2_2$, $-CH_2X^2$, $-OCX^2_3$, $-OCHX^2_2$, $-OCH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or substituted or unsubstituted $C_1$-$C_6$ alkyl. The symbols $X^1$ and $X^2$, are independently halogen. The symbols z1 and z2 are independently an integer from 0 to 4. The symbol n is an integer from 1 to 12.

In an aspect is provided a compound having the formula:

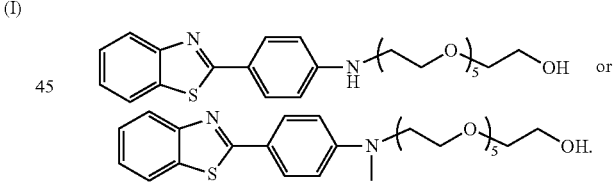

In an aspect is a pharmaceutical composition including a pharmaceutically acceptable excipient and a compound as described herein, including embodiments.

In an aspect is provided a method of increasing dendritic spine formation, increasing dendritic spine density or improving dendritic spine morphology in a subject in need thereof, the method including administering to the subject an effective amount of a compound as described herein (e.g., formula I), including embodiments.

In another aspect is provided a method of modulating the activity of a fascin protein, the method including contacting the fascin protein with an effective amount of a compound having the formula (II), including embodiments.

In another aspect is provided a method of binding a fascin protein, the method including contacting the fascin protein with an effective amount of a compound having the formula (II), including embodiments.

In an aspect is provided a method of treating cancer in a patient in need of such treatment, the method including administering a therapeutically effective amount of a compound to the patient, wherein the compound has the formula (II), including embodiments.

In an aspect is provided a method of treating a neuronal disease in a patient in need of such treatment, the method including administering a therapeutically effective amount of a compound to the patient, wherein the compound has the formula (II), including embodiments.

BRIEF DESCRIPTION OF THE DRAWINGS

(FIG. 3A) Fluorescence emission properties of BAM 1-3 and BTA-EG$_6$ in water, octanol, or an aqueous solution of liposomes. (FIG. 3B) Viability of SH-SY5Y human neuroblastoma cells as a function of increasing concentration of BTA-EG$_6$ or BAM 1-3. (FIG. 3C) Table of calculated hydrophobic parameters, measured membrane partitioning properties, and IC$_{50}$ values of toxicity in SH-SY5Y cells of BAM 1-3 and BTA-EG$_6$. log P values were calculated from Molinspirations Cheminformatics Software. SASA values were calculated with PyMOL. (FIG. 3D) Representative z-slice fluorescence micrographs from the middle of the cells showing cellular internalization of BTA-EG$_6$ and BAM 1-3 in differentiated SH-SY5Y cells. Scale bar, 25 µm.

(FIG. 5A) Representative spine segments (23 microns) for BTA-EG$_x$ and BAM 1-3 compared to control (0.1% DMSO). (FIG. 5B) Quantitative representation of spine number per micron for all compounds compared to control. The data is expressed as mean values±SEM, n≥54, with 3 segments from at least 21 neurons. *p<0.001, **p, <0.0001 as determined by unpaired t-test compared to control.

(FIG. 6C) Concentration-dependent effects of neurons dosed for 24 h with 1-25 µM of BAM1-EG$_6$ on spine density. (FIG. 6D) Persistence of spine density increase in cells exposed to BAM1-EG$_6$ compared to vehicle control (0.1% DMSO) over time. Neurons were dosed and then fixed at 24, 48 and 72 h. (FIG. 6E) Effects of removal of BAM1-EG$_6$ on dendritic spine number after treatment of cells for 24 h. After 24 h, BAM1-EG$_6$ was rinsed off and spine changes were monitored for an additional 24 and 48 h (48 and 72 h total time). The dendritic spine density 24 h after removal of BAM1-EG$_6$ is indistinguishable from control cells. (FIG. 6F) Effect of adding additional compound every 24 h. Neurons were dosed at 24 h (1×), 48 h (2×) and 72 h (3×) with no observable additional increase of dendritic spine density compared to the 1× dose. The data is expressed as mean values±SEM, n≥54, with 3 segments from at least 21 neurons. **p≤0.0001, n.s.=not significant, as determined by unpaired t-test compared to control.

(FIG. 7B) Quantitative representation of the total dendritic spines gained or lost per 20 micron segments for either BAM1-EG$_6$ or vehicle control. N=6 segments from 3 separate trials and 2 different neurons per trial. *p<0.01 compared to control at same time point by unpaired t-test.

(FIG. 8A) Representative spine segments (23 microns) of primary neurons dosed with Aβ, or Aβ plus BTA-EG$_6$ or BAMs 1-3 compared to control (0.1% DMSO). (FIG. 8B) Quantitative representation of spine number per micron for all dosing experiments compared to control. The data is expressed as mean values±SEM, n=42, with 3 segments from at least 14 neurons. ## p≤0.01, as determined by unpaired t-test compared to control. *p≤0.001, *p≤0.0001 as determined by unpaired t-test compared to cells treated with Aβ alone.

DETAILED DESCRIPTION

I. Definitions

Figure 1:
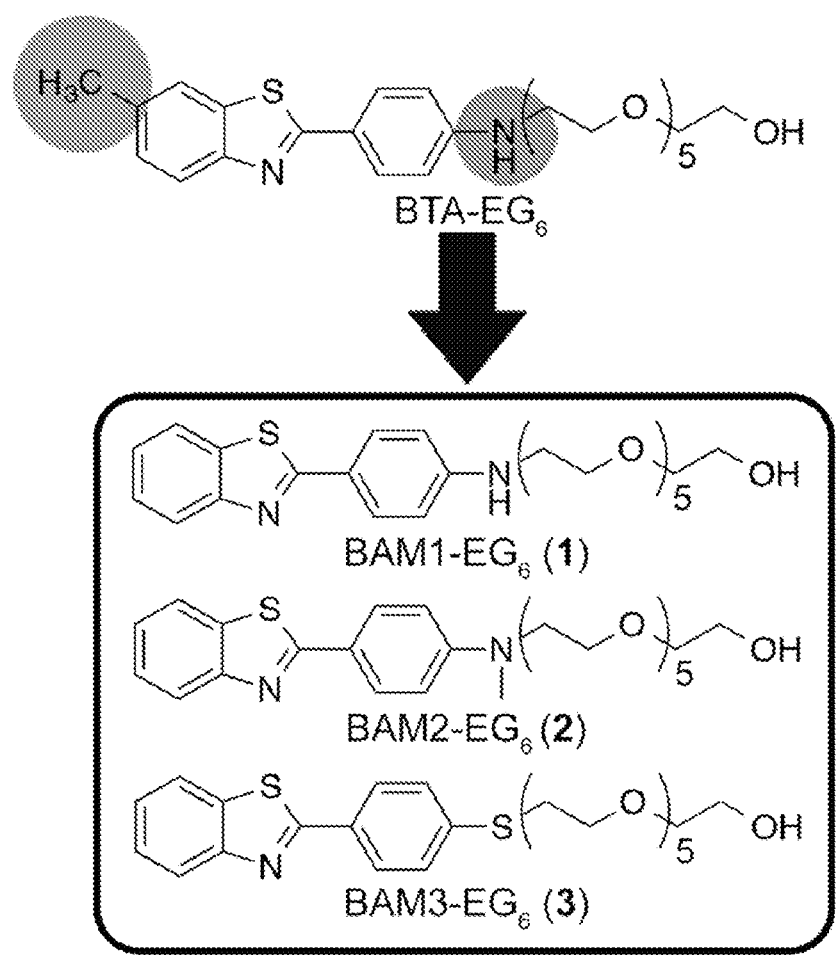
FIG. 1. Structure of benzothiazole amphiphiles (BAMs) (1-3), which exhibit decreased hydrophobicity and hydrogen-bonding capabilities compared to the parent compound, BTA-EG$_6$.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S, and wherein the nitrogen and sulfur atoms may optionally be oxidized, and the nitrogen heteroatom may optionally be quaternized). The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. In embodiments, a cycloalkyl is a spirocyclic cycloalkyl, wherein the spirocyclic rings are cycloalkyl rings. In embodiments, a cycloalkyl is a fused ring cycloalkyl, wherein the fused rings are cycloalkyl rings. In embodiments, a cycloalkyl is a bridged ring cycloalkyl, wherein the bridged rings are cycloalkyl rings. In embodiments, a cycloalkyl is monocyclic. In embodiments, a cycloalkyl is two rings. In embodiments, a cycloalkyl is three rings. In embodiments, a cycloalkyl is four rings. In embodiments, a cycloalkyl is five rings. In embodiments, a cycloalkyl is polycyclic. In embodiments, a heterocycloalkyl is a spirocyclic heterocycloalkyl, wherein the spirocyclic rings are one or more heterocycloalkyl rings and optionally one or more cycloalkyl rings. In embodiments, a heterocycloalkyl is a fused ring heterocycloalkyl, wherein the fused rings are one or more heterocycloalkyl rings and optionally one or more cycloalkyl rings. In embodiments, a heterocycloalkyl is a bridged ring heterocycloalkyl, wherein the bridged rings are one or more heterocycloalkyl rings and optionally one or more cycloalkyl rings. In embodiments, the rings of a spirocyclic, fused ring, or bridged ring heterocycloalkyl are heterocyclic rings. In embodiments, a heterocycloalkyl is monocyclic. In embodiments, a heterocycloalkyl is two rings. In embodiments, a heterocycloalkyl is three rings. In embodiments, a heterocycloalkyl is four rings. In embodiments, a heterocycloalkyl is five rings. In embodiments, a heterocycloalkyl is polycyclic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. In embodiments, an aryl is a fused ring aryl, wherein the fused rings are one or more aryl rings and optionally one or more cycloalkyl and/or heterocycloalkyl rings. In embodiments, an aryl is a bridged ring aryl, wherein the bridged rings are one or more aryl rings and optionally one or more cycloalkyl and/or heterocycloalkyl rings. In embodiments, the rings of a fused ring aryl or bridged ring aryl are aryl rings. In embodiments, an aryl is monocyclic. In embodiments, an aryl is two rings. In embodiments, an aryl is three rings. In embodiments, an aryl is four rings. In embodiments, an aryl is five rings. In embodiments, an aryl is polycyclic. In embodiments, a heteroaryl is a fused ring heteroaryl, wherein the fused rings are one or more heteroaryl rings and optionally one or more cycloalkyl, heterocycloalkyl, and/or aryl rings. In embodiments, a heteroaryl is a bridged ring heteroaryl, wherein the bridged rings are one or more heteroaryl rings and optionally one or more cycloalkyl, heterocycloalkyl, and/or aryl rings. In embodiments, the rings of a fused ring heteroaryl or bridged ring heteroaryl are heteroaryl rings. In embodiments, a heteroaryl is monocyclic. In embodiments, a heteroaryl is two rings. In embodiments, a heteroaryl is three rings. In embodiments, a heteroaryl is four rings. In embodiments, a heteroaryl is five rings. In embodiments, a heteroaryl is polycyclic. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " $\sim\!\sim$ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

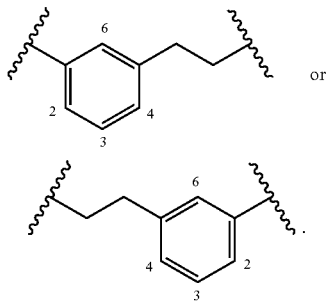

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings, bridged rings, or spirocyclic rings, a substituent depicted as associated with one member of the fused rings, bridged rings, or spirocyclic rings (a floating substituent on a single ring), may be a substituent on any of the fused rings, bridged rings, or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different bridged rings, or different spirocyclic rings, and each substituent may optionally be different. Where a point of attachment of a ring to the remainder of a molecule is not limited to a single atom (a floating substituent), the attachment point may be any atom of the ring and in the case of fused rings, bridged rings, or spirocyclic rings, any atom of any of the fused rings, bridged rings, or spirocyclic rings while obeying the rules of chemical valency. Where a ring, fused rings, bridged rings, or spirocyclic rings contain one or more ring heteroatoms and the ring, fused rings, bridged rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure and form a bridged ring structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CHF$_2$, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —OCH$_2$F, —NHSO$_2$CH$_3$, —N$_3$, unsubstituted alkyl, unsubstituted heteroalkyl, unsubstituted cycloalkyl, unsubstituted heterocycloalkyl, unsubstituted aryl, or unsubstituted heteroaryl, and (B) alkyl, heteroalkyl, cycloalkyl, heterocycloalkyl, aryl, or heteroaryl, substituted with at least one substituent selected from:

(i) oxo, halogen, —CF$_3$, —CHF$_2$, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —OCH$_2$F, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, or heteroaryl substituted with at least one substituent selected from:

(a) oxo, halogen, —CF$_3$, —CHF$_2$, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, —OCH$_2$F, —NHSO$_2$CH$_3$, —N$_3$, unsubstituted alkyl, unsubstituted heteroalkyl, unsubstituted cycloalkyl, unsubstituted heterocycloalkyl, unsubstituted aryl, or unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CHF$_2$, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —OCH$_2$F, —NHSO$_2$CH$_3$, —N$_3$, unsubstituted alkyl, unsubstituted heteroalkyl, unsubstituted cycloalkyl, unsubstituted heterocycloalkyl, unsubstituted aryl, or unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. In embodiments, the prodrug form may include a phosphate derivative or a sugar (e.g. ribose) derivative. For example prodrugs moieties used in HCV nucleoside and nucleotide prodrugs may be added to the compounds described herein or the compounds used in methods described herein. In embodiments, prodrug moieties described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes, may be added to compounds described herein or used in methods described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease (e.g., cancer or neuronal disease), pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, electrocardiogram, echocardiography, radio-imaging, nuclear scan, and/or stress testing, neuropsychiatric exams, and/or a psychiatric evaluation. For example, certain methods herein treat a neurodegenerative disease or a cancer.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. a protein associated disease, a symptom associated with a neuronal disease, or cancer) means that the disease is caused by (in whole or in part), or a symptom of the disease is caused by (in whole or in part) the substance or substance activity or function.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein (e.g., fascin) or enzyme.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein).

The term "modulator" refers to a composition that increases or decreases the level of a target molecule or structure (e.g., neuronal spines) or the function of a target molecule or structure (e.g., neuronal spines).

"Patient" or "subject in need thereof" or "subject" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human. In embodiments, a subject is human.

"Disease," "disorder" or "condition" refer to a state of being or health status of a patient or subject capable of being treated with a compound, pharmaceutical composition, or method provided herein. In embodiments, the disease is a disease related to (e.g. characterized by) an accumulation of amyloid plaques. In embodiments, the disease is a neuronal disease.

As used herein, the terms "neurodegenerative disease" or "neuronal disease" refers to a disease or condition in which the function of a subject's nervous system becomes impaired. Examples of neuronal diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), spongiform encephalopathy (e.g., Bovine Spongiform Encephalopathy (mad cow disease), Kuru, Creutzfeldt-Jakob disease, and Fatal Familial Insomnia), Canavan disease, Cockayne syndrome, Corticobasal degeneration, Creutzfeldt-Jakob disease, fragile X syndrome, frontotemporal dementia, Gerstmann-Sträussler-Scheinker syndrome, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson's disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease. In embodiments, the neuronal disease is Alzheimer's disease, Parkinson's disease, autism, stroke, post-traumatic stress disorder (PTSD), traumatic brain disorder (TBD), chronic traumatic encephalopathy (CTE), schizophrenia, dementia (e.g., general dementia), attention-deficit/hyperactivity disorder (ADHD), amyotrophic lateral sclerosis (ALS), frontotemporal lobar degeneration (FTLD) (e.g., FTLD-tau, FTLD-TDP, or FTLD-FUS), memory loss (e.g., age-related memory loss), hypertensive encephalopathy, or chronic stress. In embodiments, the neuronal disease is Alzheimer's disease, Parkinson's disease, autism, post-traumatic stress disorder (PTSD), traumatic brain disorder (TBD), chronic traumatic encephalopathy (CTE), schizophrenia, dementia (e.g., general dementia), attention-deficit/hyperactivity disorder (ADHD), amyotrophic lateral sclerosis (ALS), frontotemporal lobar degeneration (FTLD) (e.g., FTLD-tau, FTLD-TDP, or FTLD-FUS), memory loss (e.g., age-related memory loss), hypertensive encephalopathy.

Alzheimer's disease is characterized by symptoms of memory loss in the early stages of the disease. As the disease advances, symptoms include confusion, long-term memory loss, paraphasia, loss of vocabulary, aggression, irritability and/or mood swings. In more advanced stages of the disease, there is loss of bodily functions. In embodiments the neuronal disease is Fragile-X syndrome (FXS). As known in the art, FXS is a genetic syndrome which has been linked to a variety of disorders (e.g., autism and inherited intellectual disability). The disability can present in a spectrum of values ranging from mild to severe. It is observed that males with FXS begin developing progressively more severe problems, typically starting after age 40, in performing tasks which require working memory. This is especially observed with respect to verbal working memory. In embodiments, the neuronal disease is autism. As known in the art, autism is a disorder of neural development. Without wishing to be bound by any theory, it is believed that autism affects information processing in the brain by altering how nerves and synapses connect and organize.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional compounds.

The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In embodiments, co-administration includes administering one active agent (e.g., compounds described herein) within 0.5, 1, 2, 4, 6, 8, 10, 12, 16, 20, or 24 hours of a second active agent (e.g., an additional anti-cancer agent). Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds described herein may be combined with treatments for neurodegeneration such as surgery.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

As used herein, the term "cancer" refers to all types of cancer, neoplasm or malignant tumors found in mammals (e.g. humans), including leukemia, melanoma, carcinomas, and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, or trilateral retinoblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The compounds described herein can be used in combination with one another, with other active agents known to be useful in treating cancer, or with adjunctive agents that may not be effective alone, but may contribute to the efficacy of the active agent.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a fascin protein with a compound as described herein may reduce the level of a product of the fascin protein catalyzed reaction or the level of a downstream derivative of the product or binding may reduce the interactions between the fascin protein or a fascin protein reaction product and downstream effectors or signaling pathway components, resulting in changes in cell growth, proliferation, or survival.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

The term "fascin" refers to a 54-58 kDa protein that is an actin cross-linking protein. The term "fascin" may refer to the nucleotide sequence or protein sequence of human fascin (e.g., Entrez 6624, OMIM 602689, Uniprot Q16658, RefSeq NM_003088; or RefSeq NP_003079) The term "fascin" includes both the wild-type form of the nucleotide sequences or proteins as well as any mutants thereof. In some embodiments, "fascin" is wild-type fascin. In some embodiments, "fascin" is one or more mutant forms. In embodiments, a fascin is human fascin. In embodiments, the fascin has the nucleotide sequence corresponding to reference number GI:347360903. In embodiments, the fascin has the nucleotide sequence corresponding to RefSeq NM_003088.3. In embodiments, the fascin has the protein sequence corresponding to RefSeq NP_003079.1.

The term "spinogenesis" and the like refer, in the usual and customary sense, to development (e.g. growth and/or maturation) of dendritic spines in neurons. In embodiments, the compounds provided herein promote spinogenesis without affecting spine morphology. The promotion is relative to the absence of administration of the compound.

The term "in vitro" is used in accordance with its ordinary meaning and refers to being outside of a living organism (e.g., human) (e.g., in the context of a process (e.g., method) or complex (e.g., compound-protein conjugate). For example, an in vitro compound is a compound in a laboratory vesicle (e.g., test tube, petri dish, or flask).

Figure 5A:
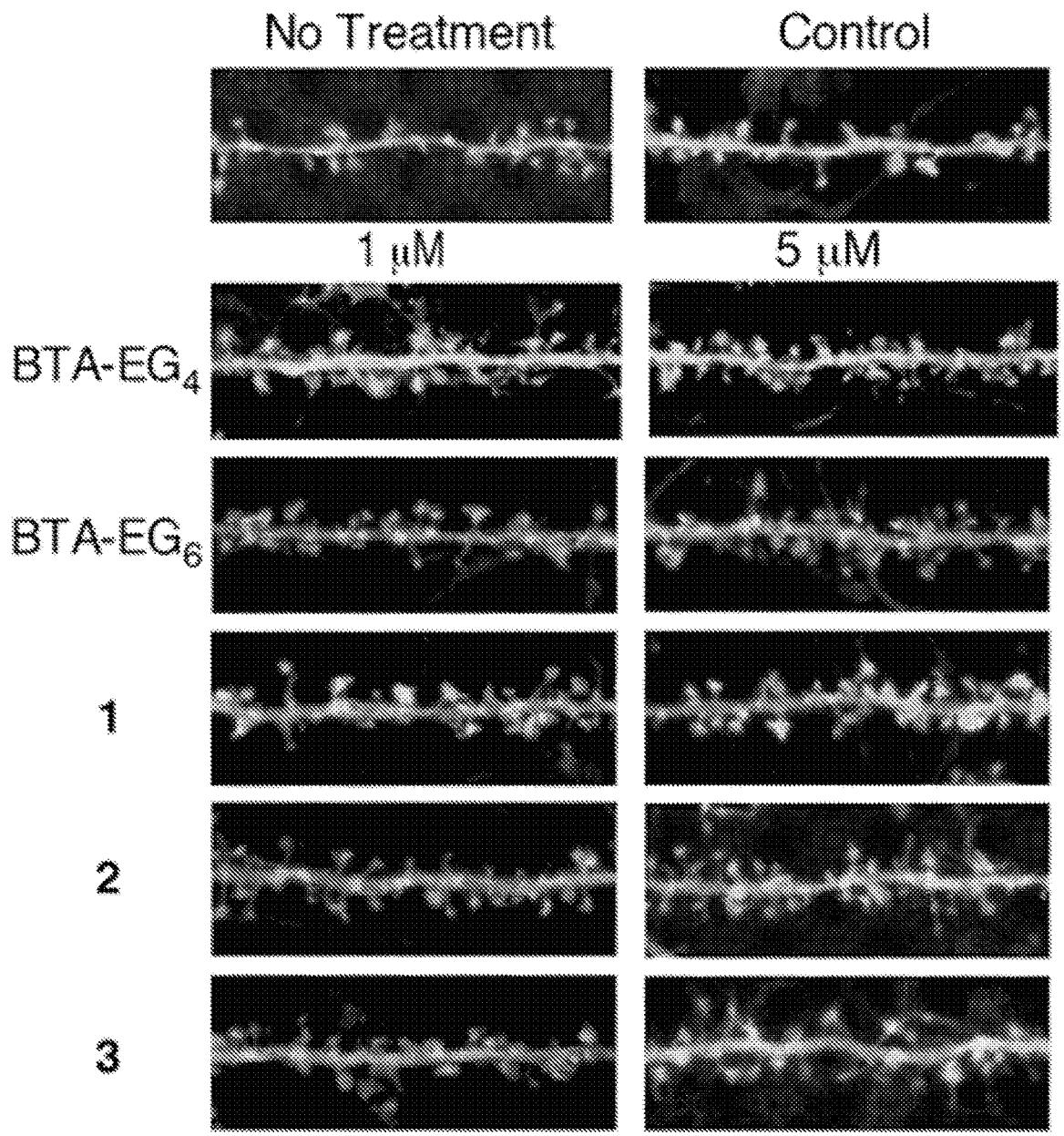
FIGS. 5A-5B. Spinogenic properties of BTA-EG$_x$ and BAMs 1-3 observed in rat primary hippocampal neurons.
Figure 5B:
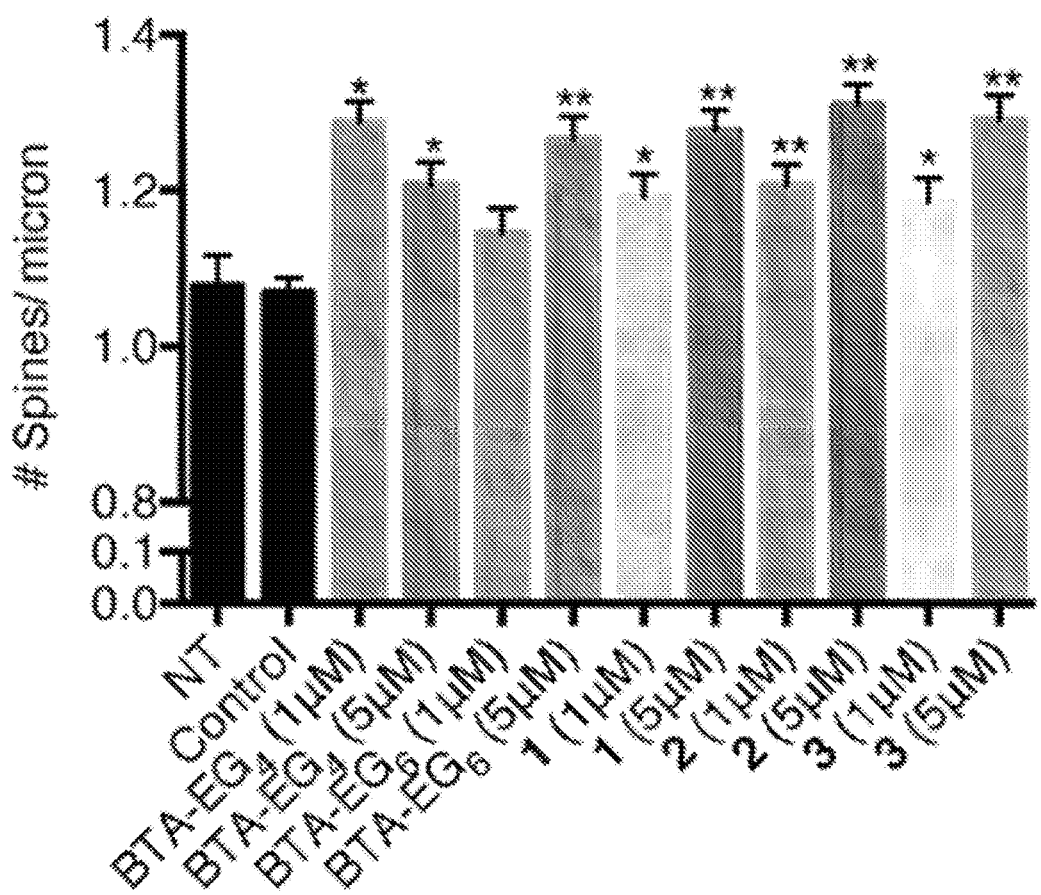

As used herein, the term "dendrite" refers to the branched extension of a neuron cell. Dendrites are typically responsible for receiving electrochemical signals transmitted from the axon of a surrounding neuron. The terms "dendritic spines" or "dendrite spines" refer to protoplasmic protuberances on a neuron cell (e.g., on a dendrite). In embodiments, dendritic spines may be described as having a membranous neck which may be terminated with a capitulum (e.g., head), which are classified according to their shape: headless, thin, stubby, mushroom, or branched. Dendritic spinal density therefore refers to the total number of dendritic spines per unit length of a neuron cell. For example, the dendritic spine density may be reported as the number of dendritic spines per micron, as indicated in FIG. 5B. Further information about dendritic spines may be found in Koch and Zador, J.

Journal of Neuroscience 1 Feb. 1993, 13 (2) 413-422, which is incorporated herein in its entirety for all purposes.

The term "dendritic spine formation" and the like refer, in the usual and customary sense to processes which lead to an increased number of dendritic spines or increased development of dendritic spines. The term "dendritic spine morphology" and the like refer, in the usual and customary sense, to physical characterization of a dendritic spine (e.g., shape and structure). Improvement of dendritic spine morphology is a change in morphology (e.g., increase in length or increase in width) that results in increased functionality (e.g., increased number of contacts between neurons or decreased space between neighboring neurons (e.g., synaptic cleft)). As known in the art and disclosed herein, exemplary methods for such characterization include measurement of the dimensions (i.e., length and width) of dendritic spines. Accordingly, the term "improving dendritic spine morphology" generally refers to an increase in length, width, or both length and width of a dendritic spine.

"Binding" is used in accordance with its plain ordinary meaning and refers to the process of allowing at least two distinct species (e.g. chemical compounds including biomolecules, or cells) to become sufficiently proximal to react or interact thereby resulting in the formation of a molecular complex. For example, the binding of two distinct species (e.g., a protein and a compound described herein) may result in the formation of a molecular complex wherein the species are interacting via non-covalent or covalent bonds. In embodiments, the resulting molecular complex is formed when two distinct species (e.g., a protein and a compound described herein) interact via non-covalent bonds (e.g., electrostatic, van der Waals, or hydrophobic).

II. Compounds

In an aspect, is provided a compound having the formula (I):

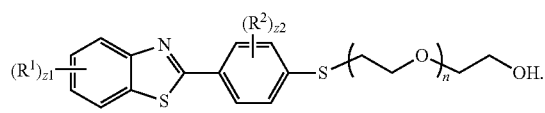

(I)

$R^1$ is independently halogen, —$CX^1_3$, —$CHX^1_2$, —$CH_2X^1$, —$OCX^1_3$, —$OCHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, —$CX^2_3$, —$CHX^2_2$, —$CH_2X^2$, —$OCX^2_3$, —$OCHX^2_2$, —$OCH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols $X^1$ and $X^2$ are independently halogen. The symbols z1 and z2 are independently an integer from 0 to 4. The symbol n is an integer from 1 to 20.

In another aspect is a complex (e.g., an in vitro complex) including a fascin protein non-covalently bound to a compound having the formula (II):

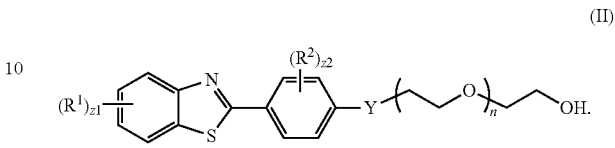

(II)

The symbol Y is —$NR^3$— or —S—. $R^1$ is independently halogen, —$CX^1_3$, —$CHX^1_2$, —$CH_2X^1$, —$OCX^1_3$, —$OCHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, —$CX^2_3$, —$CHX^2_2$, —$CH_2X^2$, —$OCX^2_3$, —$OCHX^2_2$, —$OCH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or substituted or unsubstituted $C_1$-$C_6$ alkyl. The symbols $X^1$ and $X^2$, are independently halogen. The symbols z1 and z2 are independently an integer from 0 to 4. The symbol n is an integer from 1 to 20.

In embodiments, Y is —$NR^3$—. In embodiments, Y is —N(CH$_3$)—. In embodiments, Y is —NH—. In embodiments, Y is —S—.

In embodiments, $R^1$ is independently halogen, —$CX^1_3$, —$CHX^1_2$, —$CH_2X^1$, —$OCX^1_3$, —$OCHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$ is an unsubstituted $C_1$-$C_6$ alkyl. In embodiments, $R^1$ is —$CH_3$.

In embodiments, $R^1$ is independently halogen, —$CX^1_3$, —$CHX^1_2$, —$CH_2X^1$, —$OCX^1_3$, —$OCHX^1_2$, —$OCH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted (e.g., substituted with substituent group(s), size-limited substituent group(s), or lower substituent group(s)) or unsubstituted alkyl, substituted (e.g., substituted with substituent group(s), size-limited substituent group(s), or lower substituent group(s)) or unsubstituted heteroalkyl, substituted (e.g., substituted with substituent group(s), size-limited substituent group(s), or lower substituent group(s)) or unsubstituted cycloalkyl, substituted (e.g., substituted with substituent group(s), size-limited substituent group(s), or lower substituent group(s)) or unsubstituted heterocycloalkyl, substituted (e.g., substituted with substituent group(s), size-limited substituent group(s), or lower substituent group(s)) or unsubstituted aryl, or substituted (e.g., substituted with substituent group(s), size-limited substituent group(s), or lower substituent group(s)) or unsubstituted heteroaryl. In embodiments, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is substituted or unsubstituted alkyl.

In embodiments, $R^1$ is independently halogen, $-CX^1_3$, $-CHX^1_2$, $-CH_2X^1$, $-OCX^1_3$, $-OCHX^1_2$, $-OCH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is substituted (e.g., substituted with substituent group(s), size-limited substituent group(s), or lower substituent group(s)) or unsubstituted alkyl. In embodiments, $R^1$ is substituted (e.g., substituted with substituent group(s), size-limited substituent group(s), or lower substituent group(s)) alkyl. In embodiments, $R^1$ is unsubstituted alkyl. In embodiments, $R^1$ is substituted or unsubstituted alkyl (e.g., $C_1$-$C_8$, $C_1$-$C_6$, $C_1$-$C_4$, or $C_1$-$C_2$). In embodiments, $R^1$ is substituted alkyl (e.g., $C_1$-$C_8$, $C_1$-$C_6$, $C_1$-$C_4$, or $C_1$-$C_2$). In embodiments, $R^1$ is unsubstituted alkyl (e.g., $C_1$-$C_8$, $C_1$-$C_6$, $C_1$-$C_4$, or $C_1$-$C_2$). In embodiments, $R^1$ is unsubstituted $C_1$-$C_2$ alkyl.

In embodiments, $R^1$ is substituted (e.g., substituted with substituent group(s), size-limited substituent group(s), or lower substituent group(s)) or unsubstituted heteroalkyl. In embodiments, $R^1$ is substituted (e.g., substituted with substituent group(s), size-limited substituent group(s), or lower substituent group(s)) heteroalkyl. In embodiments, $R^1$ is unsubstituted heteroalkyl. In embodiments, $R^1$ is substituted or unsubstituted heteroalkyl (e.g., 2 to 8 membered, 2 to 6 membered, 4 to 6 membered, 2 to 3 membered, or 4 to 5 membered). In embodiments, $R^1$ is substituted heteroalkyl (e.g., 2 to 8 membered, 2 to 6 membered, 4 to 6 membered, 2 to 3 membered, or 4 to 5 membered). In embodiments, $R^1$ is an unsubstituted heteroalkyl (e.g., 2 to 8 membered, 2 to 6 membered, 4 to 6 membered, 2 to 3 membered, or 4 to 5 membered).

In embodiments, $R^1$ is substituted (e.g., substituted with substituent group(s), size-limited substituent group(s), or lower substituent group(s)) or unsubstituted cycloalkyl. In embodiments, $R^1$ is substituted (e.g., substituted with substituent group(s), size-limited substituent group(s), or lower substituent group(s)) cycloalkyl. In embodiments, $R^1$ is an unsubstituted cycloalkyl. In embodiments, $R^1$ is substituted or unsubstituted cycloalkyl (e.g., $C_3$-$C_8$, $C_3$-$C_6$, $C_4$-$C_6$, or $C_5$-$C_6$). In embodiments, $R^1$ is substituted cycloalkyl (e.g., $C_3$-$C_8$, $C_3$-$C_6$, $C_4$-$C_6$, or $C_5$-$C_6$). In embodiments, $R^1$ is unsubstituted cycloalkyl (e.g., $C_3$-$C_8$, $C_3$-$C_6$, $C_4$-$C_6$, or $C_5$-$C_6$).

In embodiments, $R^1$ is substituted (e.g., substituted with substituent group(s), size-limited substituent group(s), or lower substituent group(s)) or unsubstituted heterocycloalkyl. In embodiments, $R^1$ is substituted (e.g., substituted with substituent group(s), size-limited substituent group(s), or lower substituent group(s)) heterocycloalkyl. In embodiments, $R^1$ is an unsubstituted heterocycloalkyl. In embodiments, $R^1$ is substituted or unsubstituted heterocycloalkyl (e.g., 3 to 8 membered, 3 to 6 membered, 4 to 6 membered, 4 to 5 membered, or 5 to 6 membered). In embodiments, $R^1$ is substituted heterocycloalkyl (e.g., 3 to 8 membered, 3 to 6 membered, 4 to 6 membered, 4 to 5 membered, or 5 to 6 membered). In embodiments, $R^1$ an unsubstituted heterocycloalkyl (e.g., 3 to 8 membered, 3 to 6 membered, 4 to 6 membered, 4 to 5 membered, or 5 to 6 membered).

In embodiments, $R^1$ is substituted (e.g., substituted with substituent group(s), size-limited substituent group(s), or lower substituent group(s)) or unsubstituted aryl. In embodiments, $R^1$ is substituted (e.g., substituted with substituent group(s), size-limited substituent group(s), or lower substituent group(s)) aryl. In embodiments, $R^1$ is an unsubstituted aryl. In embodiments, $R^1$ is substituted or unsubstituted aryl (e.g., $C_6$-$C_{10}$ or phenyl). In embodiments, $R^1$ is substituted aryl (e.g., $C_6$-$C_{10}$ or phenyl). In embodiments, $R^1$ is an unsubstituted aryl (e.g., $C_6$-$C_{10}$ or phenyl).

In embodiments, $R^1$ is substituted (e.g., substituted with substituent group(s), size-limited substituent group(s), or lower substituent group(s)) or unsubstituted heteroaryl. In embodiments, $R^1$ is substituted (e.g., substituted with substituent group(s), size-limited substituent group(s), or lower substituent group(s)) heteroaryl. In embodiments, $R^1$ is an unsubstituted heteroaryl. In embodiments, $R^1$ is substituted or unsubstituted heteroaryl (e.g., 5 to 10 membered, 5 to 9 membered, or 5 to 6 membered). In embodiments, $R^1$ is substituted heteroaryl (e.g., 5 to 10 membered, 5 to 9 membered, or 5 to 6 membered). In embodiments, $R^1$ is an unsubstituted heteroaryl (e.g., 5 to 10 membered, 5 to 9 membered, or 5 to 6 membered).

In embodiments, $R^2$ is independently halogen, $-CX^2_3$, $-CHX^2_2$, $-CH_2X^2$, $-OCX^2_3$, $-OCHX^2_2$, $-OCH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is substituted or unsubstituted alkyl.

In embodiments, $R^2$ is independently halogen, $-CX^2_3$, $-CHX^2_2$, $-CH_2X^2$, $-OCX^2_3$, $-OCHX^2_2$, $-OCH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted (e.g., substituted with substituent group(s), size-limited substituent group(s), or lower substituent group(s)) or unsubstituted alkyl, substituted (e.g., substituted with substituent group(s), size-limited substituent group(s), or lower substituent group(s)) or unsubstituted heteroalkyl, substituted (e.g., substituted with substituent group(s), size-limited substituent group(s), or lower substituent group(s)) or unsubstituted cycloalkyl, substituted (e.g., substituted with substituent group(s), size-limited substituent group(s), or lower substituent group(s)) or unsubstituted heterocycloalkyl, substituted (e.g., substituted with substituent group(s), size-limited substituent group(s), or lower substituent group(s)) or unsubstituted aryl, or substituted (e.g., substituted with substituent group(s), size-limited substituent group(s), or lower substituent group(s)) or unsubstituted heteroaryl.

In embodiments, $R^2$ is independently halogen, $-CX^2_3$, $-CHX^2_2$, $-CH_2X^2$, $-OCX^2_3$, $-OCHX^2_2$, $-OCH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is substituted (e.g., substituted with substituent group(s), size-limited substituent group(s), or lower substituent group(s)) or unsubstituted alkyl. In embodiments, $R^2$ is substituted (e.g., substituted with substituent group(s), size-limited substituent group(s), or lower substituent group(s)) alkyl. In embodiments, $R^2$ is unsubstituted alkyl. In embodiments, $R^2$ is substituted or unsubstituted alkyl (e.g., $C_1$-$C_8$, $C_1$-$C_6$, $C_1$-$C_4$, or $C_1$-$C_2$). In embodiments, $R^2$ is substituted alkyl (e.g., $C_1$-$C_8$, $C_1$-$C_6$, $C_1$-$C_4$, or $C_1$-$C_2$). In embodiments, $R^2$ is unsubstituted alkyl (e.g., $C_1$-$C_8$, $C_1$-$C_6$, $C_1$-$C_4$, or $C_1$-$C_2$). In embodiments, $R^2$ is an unsubstituted $C_1$-$C_2$ alkyl.

In embodiments, $R^2$ is substituted (e.g., substituted with substituent group(s), size-limited substituent group(s), or lower substituent group(s)) or unsubstituted heteroalkyl. In embodiments, $R^2$ is substituted (e.g., substituted with substituent group(s), size-limited substituent group(s), or lower substituent group(s)) heteroalkyl. In embodiments, $R^2$ is unsubstituted heteroalkyl. In embodiments, $R^2$ is substituted or unsubstituted heteroalkyl (e.g., 2 to 8 membered, 2 to 6 membered, 4 to 6 membered, 2 to 3 membered, or 4 to 5 membered). In embodiments, $R^2$ is substituted heteroalkyl (e.g., 2 to 8 membered, 2 to 6 membered, 4 to 6 membered, 2 to 3 membered, or 4 to 5 membered). In embodiments, $R^2$ is an unsubstituted heteroalkyl (e.g., 2 to 8 membered, 2 to 6 membered, 4 to 6 membered, 2 to 3 membered, or 4 to 5 membered).

In embodiments, $R^2$ is substituted (e.g., substituted with substituent group(s), size-limited substituent group(s), or lower substituent group(s)) or unsubstituted cycloalkyl. In embodiments, $R^2$ is substituted (e.g., substituted with substituent group(s), size-limited substituent group(s), or lower substituent group(s)) cycloalkyl. In embodiments, $R^2$ is an unsubstituted cycloalkyl. In embodiments, $R^2$ is substituted or unsubstituted cycloalkyl (e.g., $C_3$-$C_8$, $C_3$-$C_6$, $C_4$-$C_6$, or $C_5$-$C_6$). In embodiments, $R^2$ is substituted cycloalkyl (e.g., $C_3$-$C_8$, $C_3$-$C_6$, $C_4$-$C_6$, or $C_5$-$C_6$). In embodiments, $R^2$ is unsubstituted cycloalkyl (e.g., $C_3$-$C_8$, $C_3$-$C_6$, $C_4$-$C_6$, or $C_5$-$C_6$).

In embodiments, $R^2$ is substituted (e.g., substituted with substituent group(s), size-limited substituent group(s), or lower substituent group(s)) or unsubstituted heterocycloalkyl. In embodiments, $R^2$ is substituted (e.g., substituted with substituent group(s), size-limited substituent group(s), or lower substituent group(s)) heterocycloalkyl. In embodiments, $R^2$ is an unsubstituted heterocycloalkyl. In embodiments, $R^2$ is substituted or unsubstituted heterocycloalkyl (e.g., 3 to 8 membered, 3 to 6 membered, 4 to 6 membered, 4 to 5 membered, or 5 to 6 membered). In embodiments, $R^2$ is substituted heterocycloalkyl (e.g., 3 to 8 membered, 3 to 6 membered, 4 to 6 membered, 4 to 5 membered, or 5 to 6 membered). In embodiments, $R^2$ an unsubstituted heterocycloalkyl (e.g., 3 to 8 membered, 3 to 6 membered, 4 to 6 membered, 4 to 5 membered, or 5 to 6 membered).

In embodiments, $R^2$ is substituted (e.g., substituted with substituent group(s), size-limited substituent group(s), or lower substituent group(s)) or unsubstituted aryl. In embodiments, $R^2$ is substituted (e.g., substituted with substituent group(s), size-limited substituent group(s), or lower substituent group(s)) aryl. In embodiments, $R^2$ is an unsubstituted aryl. In embodiments, $R^2$ is substituted or unsubstituted aryl (e.g., $C_6$-$C_{10}$ or phenyl). In embodiments, $R^2$ is substituted aryl (e.g., $C_6$-$C_{10}$ or phenyl). In embodiments, $R^2$ is an unsubstituted aryl (e.g., $C_6$-$C_{10}$ or phenyl).

In embodiments, $R^2$ is substituted (e.g., substituted with substituent group(s), size-limited substituent group(s), or lower substituent group(s)) or unsubstituted heteroaryl. In embodiments, $R^2$ is substituted (e.g., substituted with substituent group(s), size-limited substituent group(s), or lower substituent group(s)) heteroaryl. In embodiments, $R^2$ is an unsubstituted heteroaryl. In embodiments, $R^2$ is substituted or unsubstituted heteroaryl (e.g., 5 to 10 membered, 5 to 9 membered, or 5 to 6 membered). In embodiments, $R^2$ is substituted heteroaryl (e.g., 5 to 10 membered, 5 to 9 membered, or 5 to 6 membered). In embodiments, $R^2$ is an unsubstituted heteroaryl (e.g., 5 to 10 membered, 5 to 9 membered, or 5 to 6 membered).

In embodiments, $R^3$ is hydrogen or substituted (e.g., substituted with substituent group(s), size-limited substituent group(s), or lower substituent group(s)) or unsubstituted $C_1$-$C_6$ alkyl. In embodiments, $R^3$ is hydrogen. In embodiments, $R^3$ is substituted (e.g., substituted with substituent group(s), size-limited substituent group(s), or lower substituent group(s)) or unsubstituted $C_1$-$C_6$ alkyl. In embodiments, $R^3$ is substituted (e.g., substituted with substituent group(s), size-limited substituent group(s), or lower substituent group(s)) $C_1$-$C_6$ alkyl. In embodiments, $R^3$ is an unsubstituted $C_1$-$C_6$ alkyl. In embodiments, $R^3$ is an unsubstituted $C_1$-$C_4$ alkyl. In embodiments, $R^3$ is an unsubstituted $C_1$-$C_2$ alkyl. In embodiments, $R^3$ is $-CH_3$. In embodiments, $R^3$ is hydrogen.

In embodiments, $X^1$ is F, Cl, Br, or I. In embodiments, $X^1$ is F. In embodiments, $X^1$ is Cl. In embodiments, $X^1$ is Br. In embodiments, $X^1$ is I. In embodiments, $X^2$ is F, Cl, Br, or I. In embodiments, $X^2$ is F. In embodiments, $X^2$ is Cl. In embodiments, $X^2$ is Br. In embodiments, $X^2$ is I.

In embodiments, z1 is 0. In embodiments, z1 is 1. In embodiments, z1 is 2. In embodiments, z1 is 3. In embodiments, z1 is 4. In embodiments, z2 is 0. In embodiments, z2 is 1. In embodiments, z2 is 2. In embodiments, z2 is 3. In embodiments, z2 is 4. In embodiments, z1 is 1 and z2 is 0. In embodiments, z1 is 0 or 1. In embodiments, z2 is 0 or 1.

In embodiments, n is an integer from 1 to 20. In embodiments, n is an integer from 1 to 15. In embodiments, n is an integer from 1 to 14. In embodiments, n is an integer from 1 to 13. In embodiments, n is an integer from 1 to 12. In embodiments, n is an integer from 1 to 12. In embodiments, n is an integer from 3 to 12. In embodiments, n is an integer from 3 to 10. In embodiments, n is an integer from 3 to 8. In embodiments, n is an integer from 3 to 6. In embodiments, n is an integer from 3 to 5. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10. In embodiments, n is 11. In embodiments, n is 12. In embodiments, n is 13. In embodiments, n is 14. In embodiments, n is 15. In embodiments, n is 16. In embodiments, n is 17. In embodiments, n is 18. In embodiments, n is 19. In embodiments, n is 20. In embodiments, n is 3 or 5.

In embodiments, the compound has the formula:

$$(R^1)_{z1} \text{—benzothiazole—phenyl—Y—}(CH_2CH_2O)_n\text{—OH},$$

wherein $R^1$, z1, n, and Y are as described herein.

In embodiments, the compound has the formula:

$$R^1\text{—benzothiazole—phenyl—Y—}(CH_2CH_2O)_n\text{—OH} \text{ or}$$

$$R^1\text{—benzothiazole—phenyl—Y—}(CH_2CH_2O)_n\text{—OH},$$

wherein $R^1$, n, and Y are as described herein.

In embodiments, the compound has the formula:

$$(R^1)_{z1}\text{—benzothiazole—phenyl—N}(R^3)\text{—}(CH_2CH_2O)_n\text{—OH},$$

wherein $R^1$, z1, n, and $R^3$ are as described herein. In embodiments, the compound has the formula:

$$(R^1)_{z1}\text{—benzothiazole—phenyl—S—}(CH_2CH_2O)_n\text{—OH},$$

wherein $R^1$, z1, an n are as described herein. In embodiments, the compound has the formula:

$$\text{benzothiazole—phenyl—S—}(CH_2CH_2O)_n\text{—OH},$$

wherein n is as described herein.

In embodiments, the compound has the formula:

$$\text{benzothiazole—phenyl—S—}(CH_2CH_2O)_3\text{—OH or}$$

$$\text{benzothiazole—phenyl—S—}(CH_2CH_2O)_5\text{—OH}.$$

In embodiments, the compound has the formula:

$$\text{benzothiazole—phenyl—S—}(CH_2CH_2O)_3\text{—OH}.$$

In embodiments, the compound has the formula:

$$\text{benzothiazole—phenyl—S—}(CH_2CH_2O)_5\text{—OH}.$$

In an aspect is provided a compound having the formula:

$$\text{benzothiazole—phenyl—NH—}(CH_2CH_2O)_5\text{—OH or}$$

$$\text{benzothiazole—phenyl—N}(CH_3)\text{—}(CH_2CH_2O)_5\text{—OH}.$$

In embodiments, the compound is $$\text{benzothiazole—phenyl—NH—}(CH_2CH_2O)_5\text{—OH}.$$

In embodiments, the compound is $$\text{benzothiazole—phenyl—N}(CH_3)\text{—}(CH_2CH_2O)_5\text{—OH}.$$

In embodiments, the in vitro complex including a fascin protein non-covalently bound to a compound having the formula:

$$(R^1)_{z1}\text{—benzothiazole—phenyl—Y—}(CH_2CH_2O)_n\text{—OH}$$

wherein $R^1$, z1, n, and Y are as described herein. In embodiments, the in vitro complex includes a fascin protein non-covalently bound to a compound having the formula:

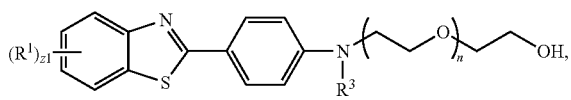

wherein $R^1$, z1, n, and $R^3$ are as described herein. In embodiments, the in vitro complex includes a fascin protein non-covalently bound to a compound having the formula:

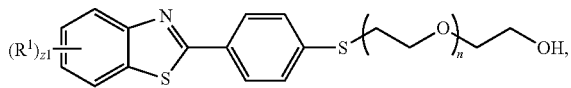

wherein $R^1$, z1, an n are as described herein. In embodiments, the in vitro complex including a fascin protein non-covalently bound to a compound having the formula:

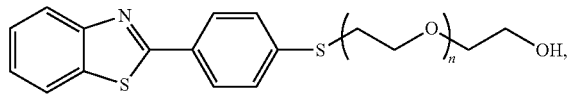

wherein n is as described herein.

In embodiments, the compounds described herein are non-toxic. In embodiments, the compounds described herein are not harmful to cells. Methods for measuring toxicity may be found in Prangkio et al. (Prangkio et al; PLoS One. 2012; 7(10): e47261.) and P. Prangkio et al. (Biochimica et Biophysica Acta 1808 (2011) 2877-2885), and are incorporated in their entirety for all purposes. In embodiments, the therapeutically effective concentration for treating a disease (e.g., a neuronal disease) is below the lethal concentration (e.g., $LD_{50}$).

In embodiments, the compounds have a solvent accessible surface area (SASA) from about 950 to about 990 $A^2$. In embodiments, the compounds have a solvent accessible surface area (SASA) from about 960 to about 990 $A^2$. In embodiments, the compounds have a solvent accessible surface area (SASA) from about 960 to about 985 $A^2$. In embodiments, the solvent accessible surface area (SASA) measurements are determined using PyMOL, as described herein. In embodiments, the compounds have a solvent accessible surface area (SASA) less than about 990 $A^2$. In embodiments, the compounds have a solvent accessible surface area (SASA) less than about 985 $A^2$.

III. Pharmaceutical Compositions

In an aspect is provided a pharmaceutical composition including a pharmaceutically acceptable excipient and a compound or a complex as described herein, including embodiments thereto. In embodiments, the pharmaceutical composition includes a pharmaceutically acceptable excipient and a compound described herein, including embodiments thereto. In embodiments, the pharmaceutical composition includes a pharmaceutically acceptable excipient and a complex as described herein, including embodiments thereto. In embodiments, the pharmaceutical composition includes an effective amount of the compound or complex (e.g., as described herein). In embodiments, the pharmaceutical composition includes a therapeutically effective amount of the compound or complex (e.g., as described herein).

In embodiments, the pharmaceutical composition is for treating a subject who has a disease (e.g., cancer or a neuronal disease) by administering to the subject a pharmaceutical composition including a therapeutically effective amount of a compound or complex described herein and a pharmaceutically acceptable excipient.

IV. Methods

In an aspect is provided a method of increasing dendritic spine formation, increasing dendritic spine density or improving dendritic spine morphology in a subject in need thereof, the method including administering to the subject an effective amount of a compound as described herein (e.g., formula I or formula II), including embodiments thereto. In embodiments, the method is increasing the dendritic spine density. In embodiments, the method includes increasing the dendritic spine density relative to a control (e.g., the absence of the administered compound). In embodiments, the method includes administering to the subject an effective amount of a compound having formula I, as described herein including embodiments.

In embodiments, the method increases dendritic spine density in primary hippocampal neurons. In embodiments, the method increases spine density through promoting the formation of new spines. In embodiments, the method increases the spinal density about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or about 100% relative to a control (e.g., the spinal density in the absence of the compound). In embodiments, the method increases the spinal density 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or 100% relative to a control (e.g., the spinal density in the absence of the compound). In embodiments, the method increases the spinal density about 30%, 35%, 40%, 45%, 50%, 55%, 60%, 65%, or about 70% relative to a control (e.g., the spinal density in the absence of the compound). In embodiments, the method increases the spinal density by at least 30%, 35%, 40%, 45%, 50%, 55%, 60%, 65%, or 70% compared to a control (e.g., the spinal density in the absence of the compound).

In embodiments, the method increases the spinal density about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, 1,000,000-fold greater relative to a control (e.g., the spinal density in the absence of the compound).

In embodiments, the method increases the spinal density 1%, 2%, 3%, 4%, 5%, 6%, 7%, 8%, 9%, 10%, 11%, 12%, 13%, 14%, 15%, 16%, 17%, 18%, 19%, or about 20% relative to a control (e.g., the spinal density in the absence of the compound). In embodiments, the method increases the spinal density 15%, 16%, 17%, 18%, 19%, or about 20% relative to a control (e.g., the spinal density in the absence of the compound). In embodiments, the method increases the spinal density about 20% relative to a control (e.g., the spinal density in the absence of the compound). In embodiments, the method increases the spinal density about 15 to 25% relative to a control (e.g., the spinal density in the absence of the compound).

In embodiments, the method increases the total number of spines per neuron. In embodiments, there are about 10, 20, 30, 40, 50, 60, 70, 80, 90, 100, 200, 300, 400, 500, 600, 700, 800, 900, or about 1000 more spines per neuron relative to a control (e.g., the number of spines in the absence of the compound).

In embodiments, the increase in spine density persists for about 4 hours following administration of an effective amount of a compound as described herein. In embodiments, the increase in spine density persists for about 8 hours following administration of an effective amount of a compound as described herein. In embodiments, the increase in spine density persists for about 12 hours following administration of an effective amount of a compound as described herein. In embodiments, the increase in spine density persists for about 16 hours following administration of an effective amount of a compound as described herein. In embodiments, the increase in spine density persists for about 24 hours following administration of an effective amount of a compound as described herein.

In embodiments, the increase in spine density persists for about 1 day following administration of an effective amount of a compound as described herein. In embodiments, the increase in spine density persists for about 1.5 days following administration of an effective amount of a compound as described herein. In embodiments, the increase in spine density persists for about 2 days following administration of an effective amount of a compound as described herein. In embodiments, the increase in spine density persists for about 2.5 days following administration of an effective amount of a compound as described herein. In embodiments, the increase in spine density persists for about 3 days following administration of an effective amount of a compound as described herein. In embodiments, the increase in spine density persists for about 3.5 days following administration of an effective amount of a compound as described herein. In embodiments, the increase in spine density persists for about 4 days following administration of an effective amount of a compound as described herein.

In embodiments, the method increases the spinal density within 1 hour following administration of an effective amount of a compound as described herein. In embodiments, the method increases the spinal density within 2 hours following administration of an effective amount of a compound as described herein. In embodiments, the method increases the spinal density within 4 hours following administration of an effective amount of a compound as described herein. In embodiments, the method increases the spinal density within 6 hours following administration of an effective amount of a compound as described herein. In embodiments, the method increases the spinal density within 8 hours following administration of an effective amount of a compound as described herein. In embodiments, the method increases the spinal density within 10 hours following administration of an effective amount of a compound as described herein. In embodiments, the method increases the spinal density within 12 hours following administration of an effective amount of a compound as described herein. In embodiments, the method increases the spinal density within 14 hours following administration of an effective amount of a compound as described herein. In embodiments, the method increases the spinal density within 16 hours following administration of an effective amount of a compound as described herein. In embodiments, the method increases the spinal density within 20 hours following administration of an effective amount of a compound as described herein. In embodiments, the method increases the spinal density within 24 hours following administration of an effective amount of a compound as described herein. In embodiments, the method increases the spinal density within 36 hours following administration of an effective amount of a compound as described herein. In embodiments, the method increases the spinal density within 48 hours following administration of an effective amount of a compound as described herein. In embodiments, the method increases the spinal density within 72 hours following administration of an effective amount of a compound as described herein. In embodiments, the method increases the spinal density within 96 hours following administration of an effective amount of a compound as described herein.

In embodiments, the method increases dendritic spine formation, increases dendritic spine density, or improves dendritic spine morphology relative to a control. In embodiments, the method increases dendritic spine formation. In embodiments, the method increases dendritic spine density. In embodiments, the method improves dendritic spine morphology.

In another aspect is provided a method of binding a fascin protein, the method including contacting the fascin protein with an effective amount of a compound having the formula (II), including embodiments thereto. In embodiments, the compound has the formula (I) as described herein, including embodiments.

In another aspect is provided a method of modulating the activity of a fascin protein, the method including contacting the fascin protein with an effective amount of a compound having the formula (II), including embodiments thereto. In embodiments, the method is inhibiting. In embodiments, the method is activating. In embodiments, the compound has the formula (I) as described herein, including embodiments.

In an aspect is provided a method of treating cancer in a patient in need of such treatment, the method including administering a therapeutically effective amount of a compound to the patient, wherein the compound has the formula (II), including embodiments thereto. In embodiments, the cancer is metastatic cancer. Metastatic cancer, is used in accordance with its ordinary meaning and refers to a cancer or neoplasm which has spread from the primary site of origin (i.e. where it originated) into different area(s) of the body. In embodiments, the method of treating cancer includes reducing the migration of cancer cells. In embodiments, the method of treating cancer includes inhibiting the migration of cancer cells. In embodiments, the method of treating cancer includes arresting (e.g., reducing or preventing) the growth of cancer cells.

In embodiments, the cancer is brain cancer. In embodiments, the cancer is glioblastoma. In embodiments, the cancer is anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme, gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, or trilateral retinoblastoma. In embodiments, the cancer expresses fascin. In embodiments, the cancer expresses detectable levels of fascin. In embodiments, the cancer expresses an increased level fascin relative to a control (e.g., normal cells, non-cancerous cells of the same cell type as the cancer cells).

In embodiments, the cancer is anaplastic astrocytoma. In embodiments, the cancer is astrocytoma. In embodiments, the cancer is central neurocytoma. In embodiments, the cancer is choroid plexus carcinoma. In embodiments, the cancer is choroid plexus papilloma. In embodiments, the cancer is choroid plexus tumor. In embodiments, the cancer is a dysembryoplastic neuroepithelial tumor. In embodiments, the cancer is an ependymal tumor. In embodiments, the cancer is fibrillary astrocytoma. In embodiments, the cancer is a giant-cell glioblastoma. In embodiments, the cancer is glioblastoma multiforme. In embodiments, the cancer is gliomatosis cerebri. In embodiments, the cancer is gliosarcoma. In embodiments, the cancer is hemangiopericytoma. In embodiments, the cancer is medulloblastoma. In embodiments, the cancer is medulloepithelioma. In embodiments, the cancer is meningeal carcinomatosis. In embodiments, the cancer is neuroblastoma. In embodiments, the cancer is neurocytoma. In embodiments, the cancer is oligoastrocytoma. In embodiments, the cancer is oligodendroglioma. In embodiments, the cancer is optic nerve sheath meningioma. In embodiments, the cancer is pediatric ependymoma. In embodiments, the cancer is pilocytic astrocytoma. In embodiments, the cancer is pinealoblastoma. In embodiments, the cancer is pineocytoma. In embodiments, the cancer is pleomorphic anaplastic neuroblastoma. In embodiments, the cancer is pleomorphic xanthoastrocytoma. In embodiments, the cancer is primary central nervous system lymphoma. In embodiments, the cancer is sphenoid wing meningioma. In embodiments, the cancer is subependymal giant cell astrocytoma. In embodiments, the cancer is subependymoma. In embodiments, the cancer is trilateral retinoblastoma.

In an aspect is provided a method of treating a neuronal disease in a patient in need of such treatment, the method including administering a therapeutically effective amount of a compound to the patient, wherein the compound has the formula (I), including embodiments thereto. In embodiments, the neuronal disease is Alzheimer's disease. In embodiments, the neuronal disease is autism. In embodiments, the neuronal disease is fragile X syndrome. In embodiments, the neuronal disease is Parkinson's disease. In embodiments, the neuronal disease includes a neuronal impairment. The term "neuronal impairment" and the like refer, in the usual and customary sense, to atrophy or other decrease in the effective functioning of the neuron. For example, it is known that Alzheimer's disease presents with neuronal impairment, especially in cortical neurons, e.g., hippocampal neurons and neurons in proximity to the hippocampus.

In embodiments, the neuronal disease is associated with abnormal dendritic spine morphology, spine size, spine plasticity, spine motility, spine density and/or abnormal synaptic function. In embodiments, the neuronal disease is associated with an abnormal (e.g., reduced) level of dendritic spine density. In embodiments, the neuronal disease is Alzheimer's disease, Parkinson's disease, autism, stroke, post-traumatic stress disorder (PTSD), traumatic brain disorder (TBD), chronic traumatic encephalopathy (CTE), schizophrenia, dementia (e.g., general dementia), attention-deficit/hyperactivity disorder (ADHD), amyotrophic lateral sclerosis (ALS), frontotemporal lobar degeneration (FTLD) (e.g., FTLD-tau, FTLD-TDP, or FTLD-FUS), memory loss (e.g., age-related memory loss), hypertensive encephalopathy, or chronic stress.

In embodiments, the neuronal disease is Alzheimer's disease. In embodiments, the neuronal disease is Parkinson's disease. In embodiments, the neuronal disease is autism. In embodiments, the neuronal disease is stroke. In embodiments, the neuronal disease is post-traumatic stress disorder (PTSD). In embodiments, the neuronal disease is traumatic brain disorder (TBD). In embodiments, the neuronal disease is chronic traumatic encephalopathy (CTE). In embodiments, the neuronal disease is schizophrenia. In embodiments, the neuronal disease is dementia (e.g., general dementia). In embodiments, the neuronal disease is attention-deficit/hyperactivity disorder (ADHD). In embodiments, the neuronal disease is amyotrophic lateral sclerosis (ALS). In embodiments, the neuronal disease is frontotemporal lobar degeneration (FTLD) (e.g., FTLD-tau, FTLD-TDP, or FTLD-FUS). In embodiments, the neuronal disease is memory loss. In embodiments, the neuronal disease includes memory loss. In embodiments, the neuronal disease is age-related memory loss. In embodiments, the neuronal disease includes age-related memory loss. In embodiments, the neuronal disease is hypertensive encephalopathy. In embodiments, the neuronal disease is chronic stress. In embodiments, the neuronal disease includes chronic stress. In embodiments, the neuronal disease is FTLD-TDP Type A. In embodiments, the neuronal disease is FTLD-TDP Type B. In embodiments, the neuronal disease is FTLD-TDP Type C. In embodiments, the neuronal disease is FTLD-TDP Type D.

In embodiments, cellular changes in brain cells contribute to pathogenesis of the neuronal disease. In embodiments, an aberrant level (e.g., reduction) in dendritic spine density in the brain contributes to the pathogenesis of the neuronal disease.

The term "memory" and the like refer, in the usual and customary sense, to the processes by which information is encoded, stored and retrieved by a subject. The terms "encode," "register" and the like in the context of memory refer, in the usual and customary sense, to receiving, processing and combining information impinging on the senses as chemical or physical stimuli. The term "stored" and the like in this context refer, in the usual and customary sense, to the creation of a record of the encoded information. The terms "retrieve," "recall" and the like in this context refer, in the usual and customary sense, to calling back the stored information. Retrieval can be in response to a cue, as known in the art. In embodiments, memory loss refers to a diminished ability to encode, store, or retrieve information.

In embodiments, the memory may be recognition memory or recall memory. In this context, "recognition memory" refers to recollection of a previously encountered stimulus. The stimulus can be e.g., a word, a scene, a sound, a smell or the like, as known in the art. A broader class of memory is "recall memory" which entails retrieval of previously learned information, e.g., a series of actions, list of words or number, or the like, which a subject has encountered previously. Methods for assessing the level of memory encoding, storage and retrieval demonstrated by a subject are well known in the art, including methods disclosed herein.

For example, in embodiments the method improves memory in a subject in need thereof, wherein the subject has a neuronal disease. In embodiments, the method improves memory in the subject. In embodiments, the method treats neuronal or cognitive impairment in the subject. In embodiments, the method treats neuronal impairment in the subject. In embodiments, the method treats cognitive impairment in the subject.

Further to any aspect disclosed herein, in embodiments the subject suffers from brain injury. Absent express indication to the contrary, the terms "brain injury" and the like refer to an insult to the brain tissue. Types of brain injury include brain damage (i.e., destruction or degeneration of brain cells), traumatic brain injury (i.e., damage accruing as the result of an external force to the brain), stroke (i.e., a vascular incident which temporarily or permanently damages the brain, e.g., via anoxia), and acquired brain injury (i.e., brain damage not present at birth). In embodiments, the method improves memory in the subject. In embodiments, the method improves learning in the subject. In embodiments, the method treats neuronal or cognitive impairment in the subject. In embodiments, the method treats neuronal impairment in the subject. In embodiments, the method treats cognitive impairment in the subject.

In embodiments, the method of treating a neuronal disease includes administering a therapeutically effective amount of a compound to the patient, wherein the compound has the formula:

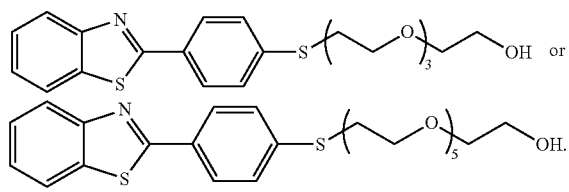

V. Embodiments

Embodiment P1

A compound with structure of Formula (II):

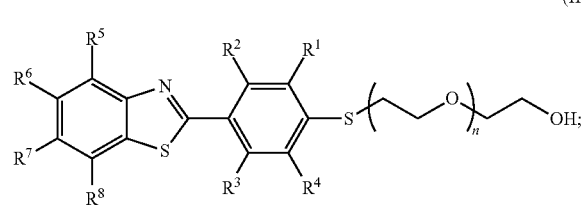

wherein $R_1$-$R_8$ are independently selected from the group consisting of hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 to 20.

Embodiment P2

A method of increasing spine density in a neuron, said method comprising contacting a neuron with a compound of Formula (I) or Formula (II),

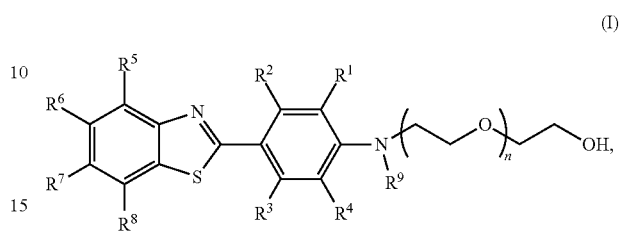

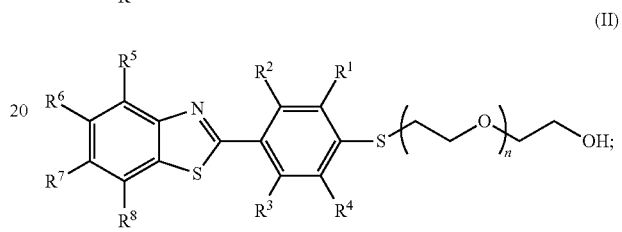

wherein $R_1$-$R_8$ are independently selected from the group consisting of hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, or substituted or unsubstituted alkyl; and n is 1 to 20.

Embodiment P3

A method of treating a disease or disorder, said method comprising administering to a subject in need an effective amount of a compound of Formula (I) or Formula (II),

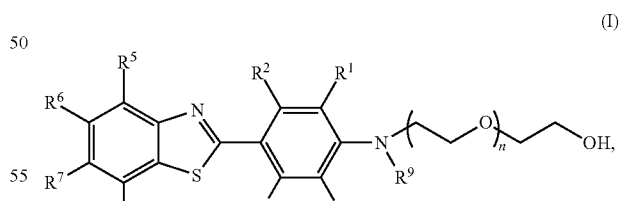

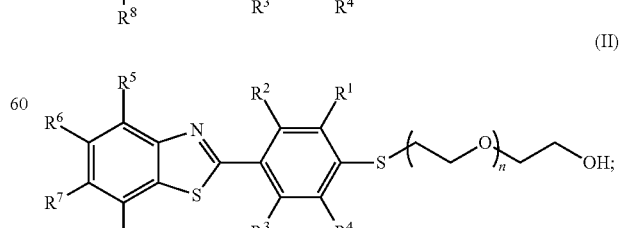

wherein

R₁-R₈ are independently selected from the group consisting of hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, or substituted or unsubstituted alkyl; and n is 1 to 20.

Embodiment P4

A pharmaceutical composition comprising a pharmaceutically acceptable excipient and a compound of Formula (I) or Formula (II),

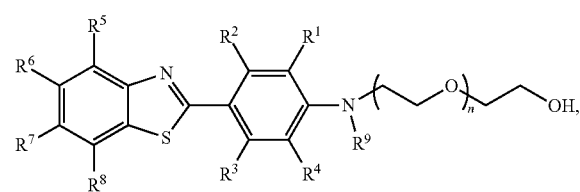

(I)

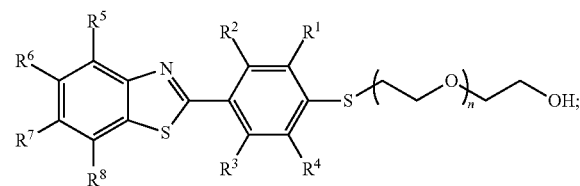

(II)

wherein

R₁-R₈ are independently selected from the group consisting of hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, or substituted or unsubstituted alkyl; and n is 1 to 20.

VI. Additional Embodiments

Embodiment 1

A compound having the formula (I):

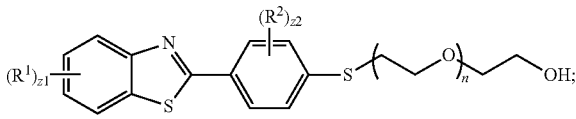

(I)

wherein

R¹ is independently halogen, —CX¹₃, —CHX¹₂, —CH₂X¹, —OCX¹₃, —OCHX¹₂, —OCH₂X¹, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is independently halogen, —CX²₃, —CHX²₂, —CH₂X², —OCX²₃, —OCHX²₂, —OCH₂X², —CN, —OH, —COOH, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X¹ and X² are independently halogen;

z1 and z2 are independently an integer from 0 to 4; and n is an integer from 1 to 12.

Embodiment 2

The compound of embodiment 1, wherein R¹ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 3

The compound of embodiment 1, wherein R¹ is substituted or unsubstituted alkyl.

Embodiment 4

The compound of any one of embodiments 1 to 3, wherein R² is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 5

The compound of any one of embodiments 1 to 3, wherein R² is substituted or unsubstituted alkyl.

Embodiment 6

The compound of any one of embodiments 1 to 5, wherein z1 is 0 or 1.

Embodiment 7

The compound of any one of embodiments 1 to 5, wherein z1 is 0.

Embodiment 8

The compound of any one of embodiments 1 to 7, wherein z2 is 0.

Embodiment 9

The compound of any one of embodiments 1 to 8, wherein n is 3 to 8.

Embodiment 10

The compound of any one of embodiments 1 to 8, wherein n is 3 to 5.

Embodiment 11

The compound of embodiment 1, having the formula:

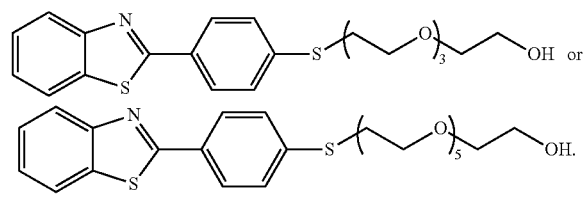

Embodiment 12

A compound having the formula:

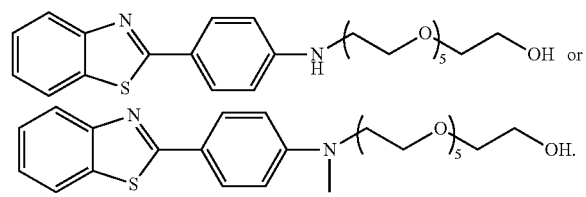

Embodiment 13

An in vitro complex comprising a fascin protein non-covalently bound to a compound having the formula (II):

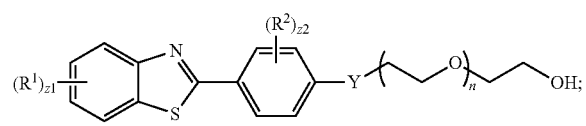

wherein
Y is —NR$^3$— or —S—;
R$^1$ is independently
halogen, —CX$^1_3$, —CHX$^1_2$, —CH$_2$X$^1$, —OCX$^1_3$, —OCHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is independently
halogen, —CX$^2_3$, —CHX$^2_2$, —CH$_2$X$^2$, —OCX$^2_3$, —OCHX$^2_2$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is hydrogen or substituted or unsubstituted C$_1$-C$_6$ alkyl;
X$^1$, X$^2$, and X$^3$ are independently halogen;
z1 is an integer from 0 to 3;
z2 is an integer from 0 to 4; and
n is an integer from 1 to 12.

Embodiment 14

A pharmaceutical composition comprising a pharmaceutically acceptable excipient and a compound of any one of embodiments 1 to 12 or a complex of embodiment 13.

Embodiment 15

A method of increasing dendritic spine formation, increasing dendritic spine density or improving dendritic spine morphology in a subject in need thereof, said method comprising administering to said subject an effective amount of a compound of any one of embodiments 1 to 12.

Embodiment 16

The method of embodiment 15, wherein said method is increasing dendritic spine density.

Embodiment 17

A method of binding a fascin protein, said method comprising contacting said fascin protein with an effective amount of a compound having the formula (II):

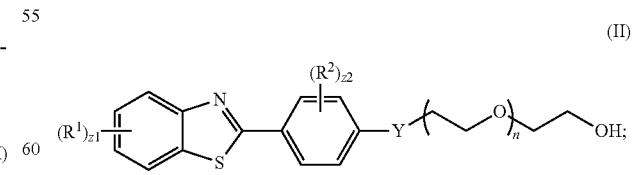

wherein
Y is —NR$^3$— or —S—;
R$^1$ is independently
halogen, —CX$^1_3$, —CHX$^1_2$, —CH$_2$X$^1$, —OCX$^1_3$, —OCHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently
halogen, —CX$^2_3$, —CHX$^2_2$, —CH$_2$X$^2$, —OCX$^2_3$, —OCHX$^2_2$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen or substituted or unsubstituted C$_1$-C$_6$ alkyl;

X$^1$ and X$^2$ are independently halogen;

z1 and z2 are independently an integer from 0 to 4; and n is an integer from 1 to 12.

Embodiment 18

A method of treating cancer in a patient in need of such treatment, said method comprising administering a therapeutically effective amount of a compound to said patient, wherein the compound has the formula (II):

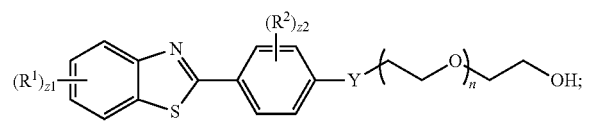

(II)

wherein
Y is —NR$^3$— or —S—;
R$^1$ is independently
halogen, —CX$^1_3$, —CHX$^1_2$, —CH$_2$X$^1$, —OCX$^1_3$, —OCHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently
halogen, —CX$^2_3$, —CHX$^2_2$, —CH$_2$X$^2$, —OCX$^2_3$, —OCHX$^2_2$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen or substituted or unsubstituted C$_1$-C$_6$ alkyl;

X$^1$ and X$^2$ are independently halogen;

z1 and z2 are independently an integer from 0 to 4; and n is an integer from 1 to 12.

Embodiment 19

A method of treating a neuronal disease in a patient in need of such treatment, said method comprising administering a therapeutically effective amount of a compound to said patient, wherein the compound is a compound of any one of claims 1 to 12.

Embodiment 20

A method of modulating the activity of a fascin protein, said method comprising contacting said fascin protein with an effective amount of a compound having the formula (II):

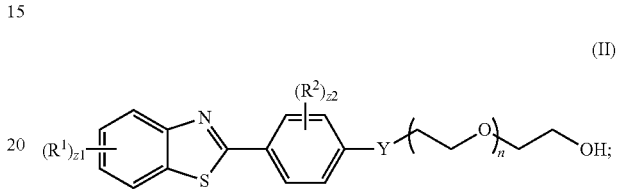

(II)

wherein
Y is —NR$^3$— or —S—;
R$^1$ is independently
halogen, —CX$^1_3$, —CHX$^1_2$, —CH$_2$X$^1$, —OCX$^1_3$, —OCHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently
halogen, —CX$^2_3$, —CHX$^2_2$, —CH$_2$X$^2$, —OCX$^2_3$, —OCHX$^2_2$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen or substituted or unsubstituted C$_1$-C$_6$ alkyl;

X$^1$ and X$^2$ are independently halogen;

z1 and z2 are independently an integer from 0 to 4; and n is an integer from 1 to 12.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Examples

A. Benzothiazole Amphiphiles Promote the Formation of Dendritic Spines in Primary Hippocampal Neurons.

Patients with Alzheimer's Disease (AD) demonstrate many characteristic neuropathies such as increased oxidative stress, mitochondrial dysfunction, synaptic dysfunction, disruption of calcium homeostasis, deposition of senile plaques and neurofibrillary tangles, and atrophy of the brain. Without wishing to be bound by any theory, it is believed that both the cause and effect of these neuropathies is the accumulation of harmful forms of aggregated Aβ peptides in the brain. Recent strategies for the treatment of AD, therefore, include controlling the production or the aggregation state of specific isoforms of Aβ peptides. Other strategies involve small molecule targeting of enzymes that play a role in production of Aβ peptides through processing of amyloid precursor protein in an attempt to lower the abundance of Aβ peptides in the brain. Additionally, there is accruing information on the role of non-amyloid neuropathies such as tauopathy or sporadic inheritance of specific mutations in the apolipoprotein E gene, which is stimulating additional strategies to combat neurodegeneration. In contrast to these strategies for therapeutic intervention, the results provided herein support a fundamentally new approach for reversing or slowing the progression of neurodegenerative diseases such as AD by promoting neurons to generate the cellular machinery required for memory retention and learning. Dendritic complexity, synaptogenesis, and overall proper development and function of neurons are regulated by growth factors such as brain derived neurotrophic factor (BDNF). While some small molecules have recently been reported to exhibit neurotrophin-like activity with respect to promoting neuritic outgrowth, none of these molecules have been demonstrated to promote dendritic spine formation.

To our knowledge, estrogen (specifically, estradiol) is the only example of a small molecule that is known to promote dendritic spine density in rodents and has been shown to improve cognition in humans. The binding of estradiol to the estrogen receptor has been shown to increase expression of BDNF in neurons, providing a mechanistic link between its cellular targeting and phenotypic activity. Estrogen hormone therapy in menopausal women below the age of 65 has been correlated with a slowing down of cognitive decline compared to placebo, with striking additional evidence of the positive effects of estrogen therapy on memory retention in surgically menopausal women. Unfortunately, the well-documented, harmful, long-term effects (e.g., increased risk of cancer, stroke and heart disease) of estrogen therapy preclude its general use for treating cognitive disorders.

The data provided herein from photoaffinity pulldown assays suggest that BTA-EG$_4$ promotes dendritic spine formation through altering the activity of fascin, which is directly involved in cytoskeletal reorganization of nascent dendritic protrusions. These results support an unprecedented molecular pathway for increasing dendritic spine density using a small molecule. The identification of new cellular targets for small molecules that lead to improved memory and learning is highly significant and can prove useful for treating many neurodegenerative and mental development disorders.

The majority of excitatory synapses in the brain exist on dendritic spines. Accordingly, the regulation of dendritic spine density in the hippocampus is thought to play a central role in learning and memory. The development of novel methods to control spine density could, therefore, have important implications for treatment of a host of neurodegenerative and developmental cognitive disorders. Herein, we report the design and evaluation of a new class of benzothiazole amphiphiles that exhibit a dose-dependent response leading to an increase in dendritic spine density in primary hippocampal neurons. Cell exposure studies reveal that the increase in spine density can persist for days in the presence of these compounds, but returns to normal spine density levels within 24 hours when the compounds are removed, demonstrating the capability to reversibly control spinogenic activity. Time-lapse imaging of dissociated hippocampal neuronal cultures shows that these compounds promote a net increase in spine density through the formation of new spines. Biochemical studies support that these compounds promote spine formation through a Ras-dependent mechanism. These spinogenic molecules were also capable of rescuing the dendritic spine loss induced by Alzheimer's-related aggregated amyloid-β peptides in primary neurons. Evaluation of this new group of spinogenic agents reveals that they also exhibit relatively low toxicity at concentrations displaying activity. Collectively, these results suggest that small molecules that promote spine formation could be potentially useful for ameliorating cognitive deficiencies associated with spine loss in neurodegenerative diseases such as Alzheimer's disease, and may also find use as general cognitive enhancers.

Dendritic spines are specialized protrusions responsible for receiving excitatory synaptic inputs, providing an important function in communication between neurons [1-3]. The morphology of dendritic spines and their overall density correlates with synaptic function and are strongly implicated in memory and learning [1,4,5]. Consequently, alteration or mis-regulation of dendritic spines can influence synaptic function and plays a major role in various neurological and psychiatric disorders such as autism, fragile X syndrome, Parkinson's Disease (PD) and Alzheimer's Disease (AD) [4,6-12]. For example, in AD there is mounting evidence suggesting deficits begin with alterations of hippocampal synaptic function caused by amyloid-β (Aβ) protein prior to neuronal loss [13-16]. Therefore, treatment strategies that target the initial synaptic loss, rather than late stage disease intervention, may provide a better prognosis for the treatment of AD. Furthermore, since most cognitive disorders elicit abnormalities in the form and function of dendritic spines, it would be desirable to target them directly using a small molecule to alter or alleviate these spine changes. For example, Fragile X syndrome is characterized by an overabundance of immature spines.

We previously reported the design, synthesis, and evaluation of two oligo(ethylene glycol) derivatives of benzothiazole aniline (BTA), BTA-EG$_6$ and BTA-EG$_4$, which exhibited a variety of advantageous properties for the potential treatment of neurodegenerative diseases such as AD [17-19]. Interestingly, BTA-EG$_4$ showed the capability to improve memory and learning in cognitive performance tests in both wild-type mice and in a mouse model for AD [18,19]. This in vivo activity of BTA-EG$_4$ was also accompanied by a phenotypic increase in dendritic spine density [18,19]. Due to the scarcity of small molecules known to increase dendritic spine density, this rare feature of benzothiazole amphiphiles is of particular interest and could be utilized as a tool to help study the relationship between spines and cognitive function.

While the in vivo properties of BTA-EG$_4$ suggest that it may provide broad therapeutic benefits for improving cognitive function in AD as well as in other dendritic spine-related diseases, [20-22] we also observed cytotoxicity of the compound in SH-SY5Y neuroblastoma cells that correlated with their ability to partition in membranes and induce membrane lysis [23]. Toxicity is one of the biggest issues at every stage of drug development [24] and the toxicity of BTA-EG$_4$ precluded our capability to adequately evaluate the extent of its spinogenic biological activity.

In order to further evaluate the ability of the benzothiazole agents to promote spinogenesis, here we designed and characterized three novel structural variants of the BTA compounds. These new benzothiazole amphiphiles (BAMs) (also referred to herein as compounds 1-3, observed in FIG. 1) exhibit substantially less toxicity compared to the parent BTA compounds. We show that these new BAM agents are capable of promoting an increase in dendritic spine density and can counteract the net spine loss induced by the presence of aggregated Aβ peptides. This spinogenic activity was dose-dependent in primary neurons, and, using BAM1-EG$_6$ (1) as a representative example, we demonstrate that the increase in spine density is reversible by removal of the compound from the cellular environment. Time-dependent imaging studies of primary neurons treated with BAM1-EG$_6$ reveal that these benzothiazoles can increase spine density through promoting the formation of new spines. Signal transduction studies support that these molecules promote spine formation by involving the activation of the Ras-ERK1/2 pathway. Taken together, these results demonstrate that these BAM agents represent new potential tools to study the relationship between dendritic spines and cognitive behavior and may open up a new avenue to explore the use of spinogenic agents for the treatment of neurodegenerative and other spine-related cognitive disorders.

Figure 2:
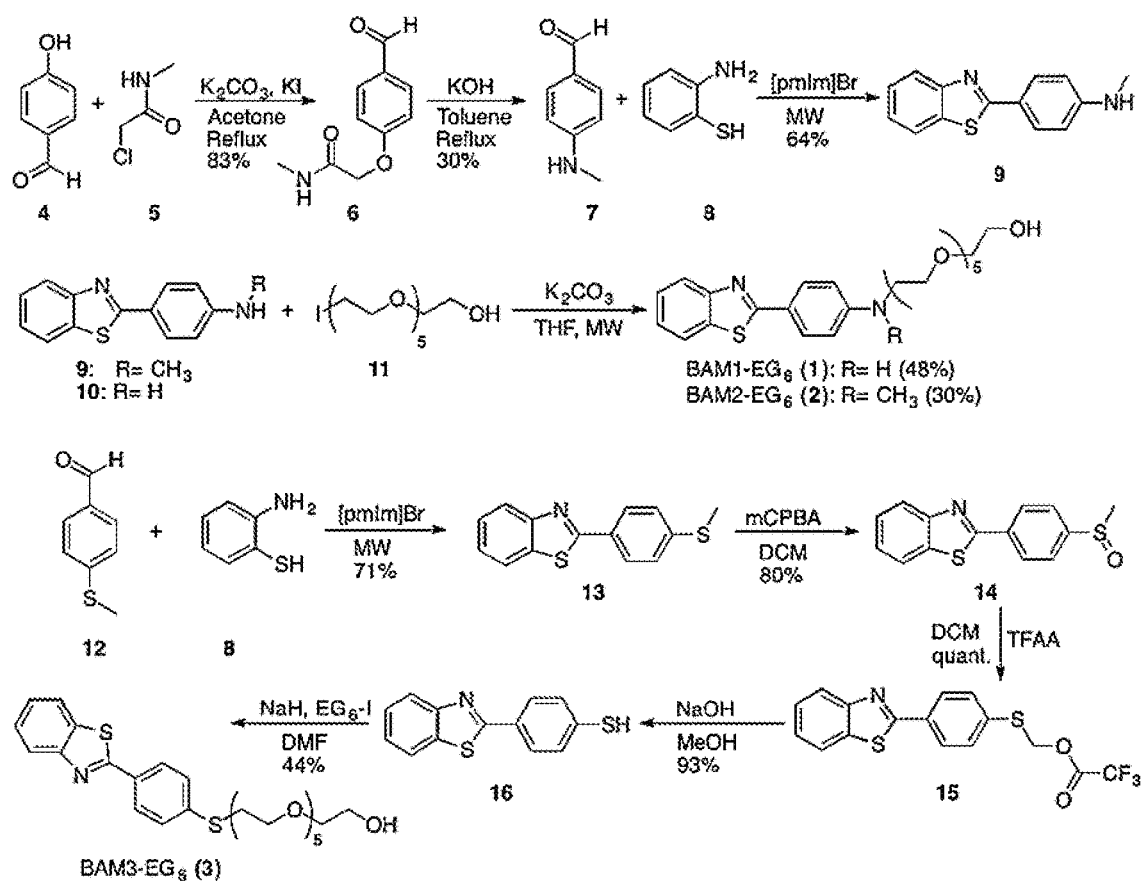
FIG. 2. Synthetic scheme for the preparation of BAM 1-3. Abbreviations for all synthetic steps are as follows: potassium carbonate (K$_2$CO$_3$), potassium iodide (KI), potassium hydroxide (KOH), ionic liquid or 1-pentyl-3-methylimidazolium bromide ([pmIm]Br), microwave (MW), tetrahydrofuran (THF), meta-chloroperoxybenzoic acid (mCPBA), dichloromethane (DCM), trifluoroacetic anhydride (TFAA), sodium hydroxide (NaOH), methanol (MeOH), sodium hydride (NaH), dimethylformamide (DMF), 17-iodo-3,6,9,12,15-pentaoxaheptadecan-1-ol (EG$_6$-I).

Design and evaluation of benzothiazole amphiphiles (BAMs) 1-3 with decreased partitioning in membranes compared to BTA-EG$_6$. The toxicity of BTA-EG$_x$ agents were previously reported to correlate with their capability to partition in membranes [23]. We hypothesized that altering the hydrophobic core of these molecules would decrease their energetic driving force to partition into membranes, thereby reducing their concomitant toxicity. To test this hypothesis, we used BTA-EG$_6$ as a lead compound for the design of three new compounds 1-3 (FIG. 1 and FIG. 2). We designed these new benzothiazoles to test whether moving the 6-methyl group in BTA-EG$_6$ to the aniline nitrogen or complete removal of the 6-methyl group would reduce the hydrophobicity of the compounds enough to significantly reduce membrane partitioning and toxicity to cells. We also tested the importance of retaining the aniline nitrogen in 1 by modifying it to a sulfur group as in BAM3-EG$_6$ (3).

Calculations (FIG. 3C) suggested that small modifications to BTA-EG$_6$ could affect its hydrophobic character as determined by their octanol-water partitioning coefficient (log P) and their solvent accessible surface area (SASA) without the need to modify the core benzothiazole structure, which is presumably required to impart spinogenic properties.

Figure 3A:
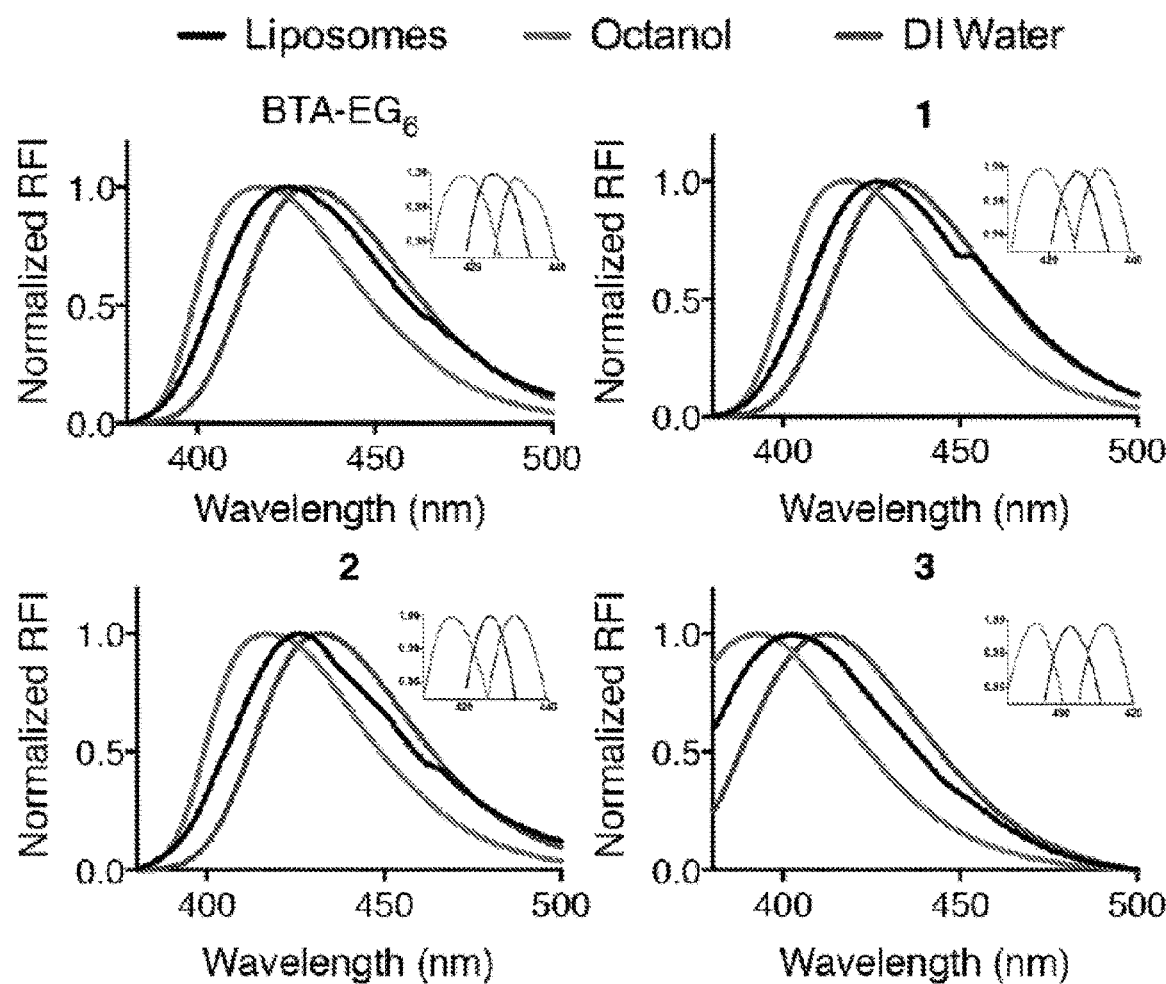
FIGS. 3A-3D. Physical and toxic properties of BAM 1-3 and BTA-EG$_6$.
Figures 3B, 3C:
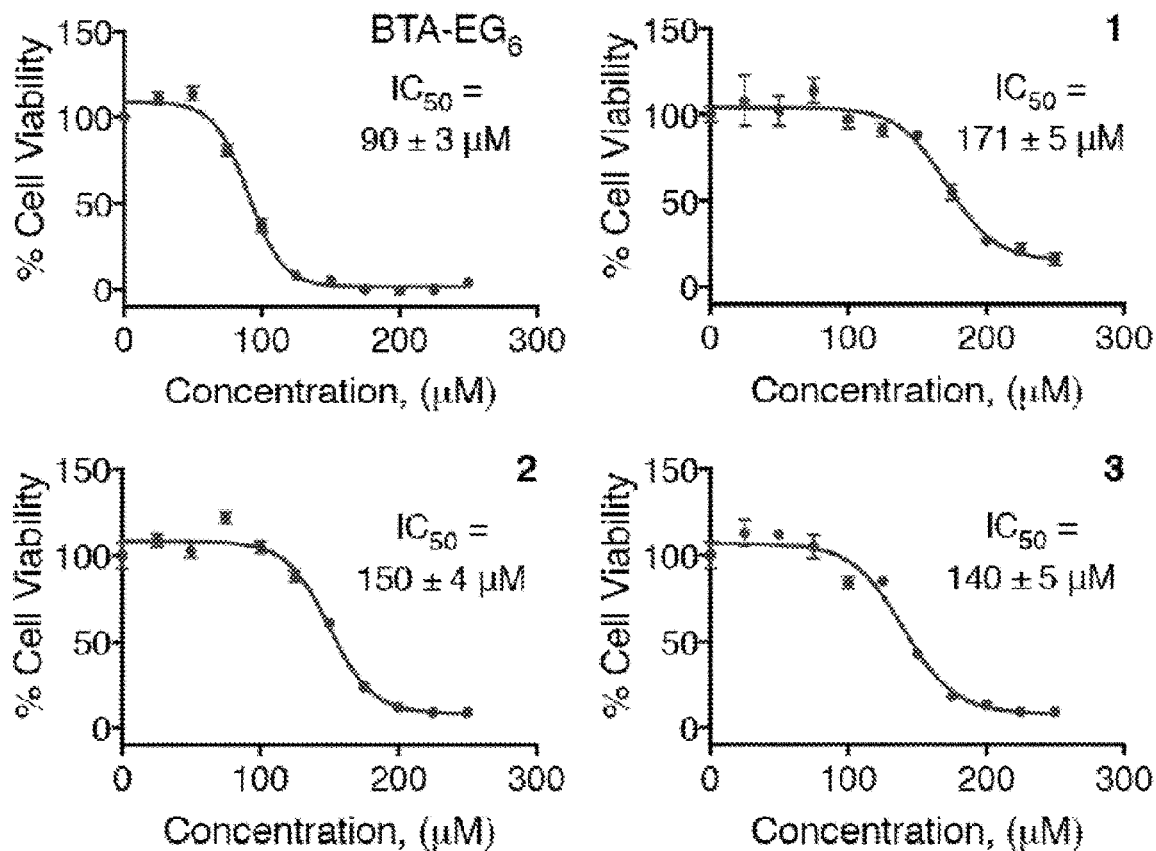

In addition to the calculated structural evaluation, we examined the hydrophobic character of the new BAMs 1-3 relative to the parent compound, BTA-EG$_6$, by taking advantage of the solvatochromic nature of these compounds. In this assay, the fluorescence emission spectra were measured for each compound in octanol, water and an aqueous suspension of liposomes to mimic cell membranes. All compounds exhibited a shift of maximum fluorescence emission to shorter wavelengths in a more hydrophobic environment (i.e., in octanol compared to water) (FIGS. 3A, 3C). The emission maximum in an aqueous suspension of liposomes was measured for all compounds and it was found that compounds 1-3 exhibited $\lambda_{max}$ that reflected a more polar, water-like environment compared to BTA-EG$_6$, with changes of emission max of 29-34% from water (relative to $\lambda_{max}$ in pure octanol) compared to a 50% change in $\lambda_{max}$ for BTA-EG$_6$ (FIGS. 3A, 3C). These results demonstrate that the novel structural modifications in BAMs 1-3 decreased their membrane partitioning over BTA-EG$_6$.

Figure 3D:
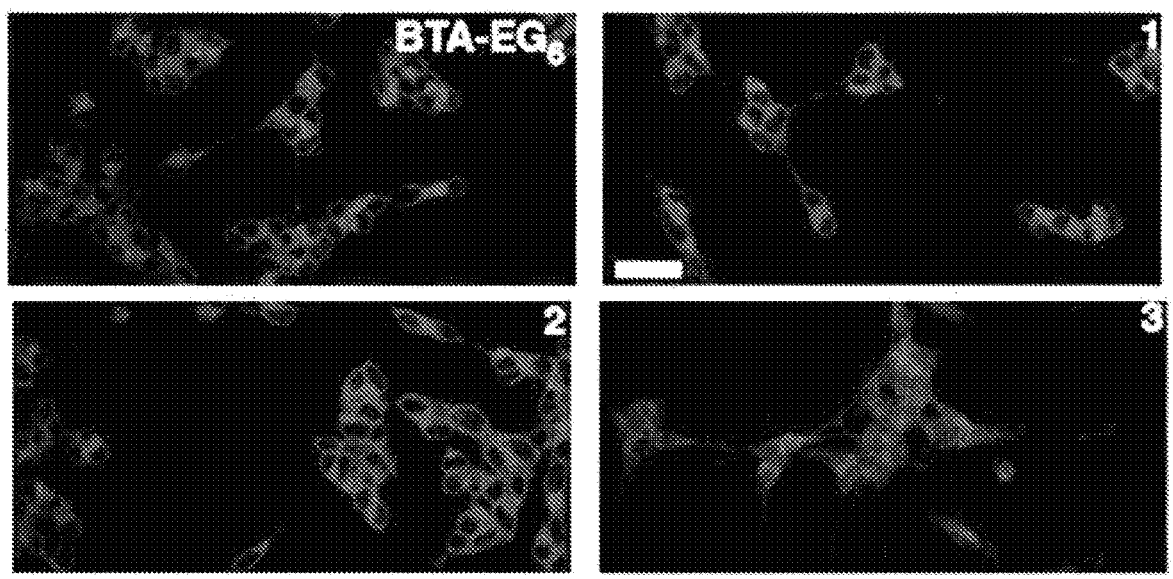

BAMs 1-3 exhibit a decreased toxicity compared to BTA-EG$_6$. An MTT cell proliferation assay was performed to compare the toxicity of compounds 1-3 to the parent compound, BTA-EG$_6$. In this assay, BTA-EG$_6$ exhibited moderate toxicity to SH-SY5Y cells with an IC$_{50}$ of 90 μM after 24 h exposure (FIGS. 3B-3C). Satisfyingly, we found that all BAMs 1-3 were significantly less toxic than BTA-EG$_6$, with IC$_{50}$'s ranging from 140-170 μM (FIGS. 3B, 3C). Visual inspection of the intrinsic fluorescence of these benzothiazole derivatives suggested that all compounds 1-3 readily internalize in cells without any obvious subcellular localization (FIG. 3D).

Figure 4:
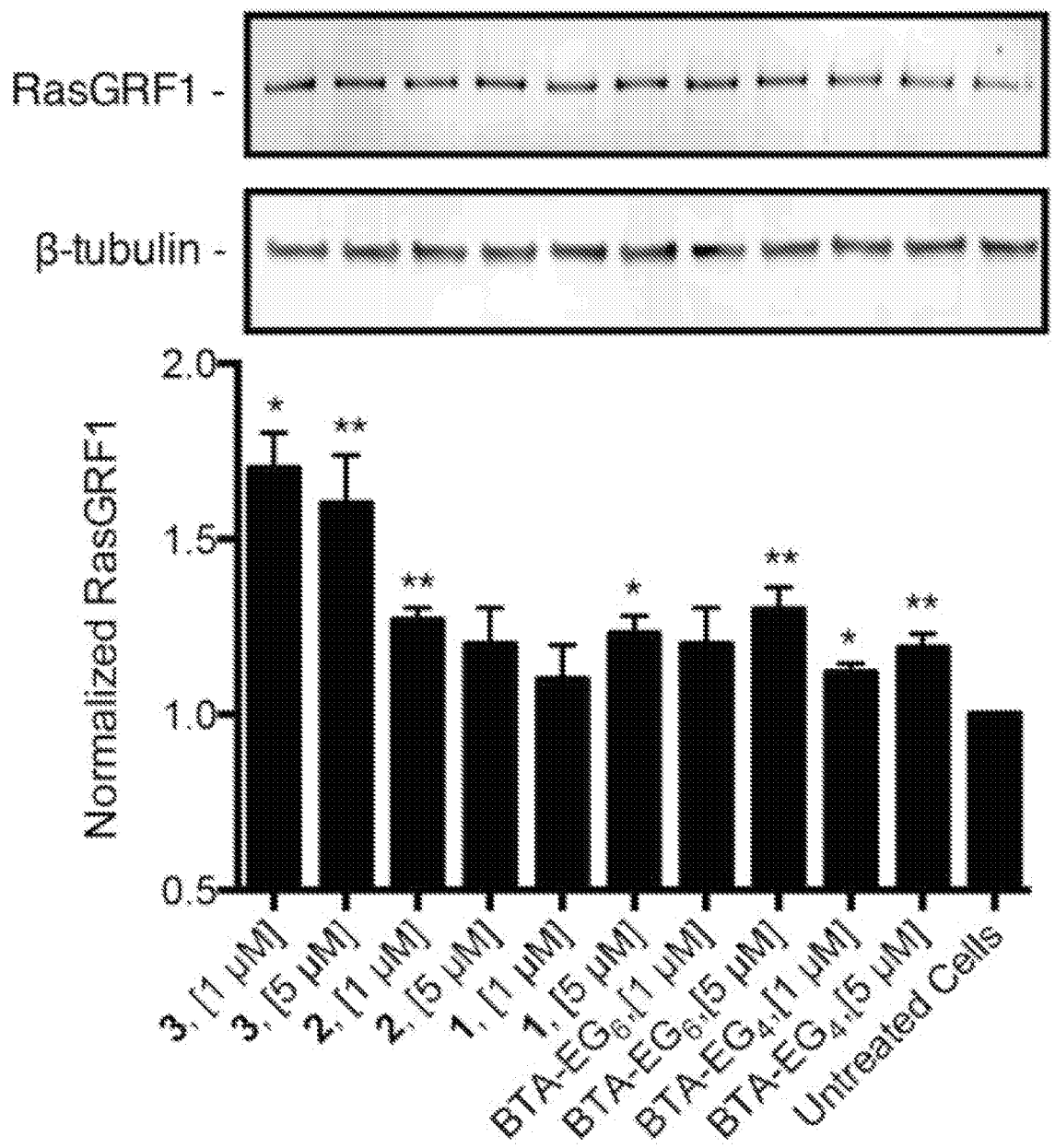
FIG. 4. Relative expression levels of RasGRF1 in differentiated SH-SY5Y cells upon dosing with 1 or 5 µM of BTA-EG$_4$, BTA-EG$_6$ and BAM 1-3. Relative RasGRF1 (145 kDa) was compared to untreated cells and all samples were normalized to loading control β-tubulin (55 kDa). The data is expressed as mean values±SEM, n=3 or more for each concentration. *, p<0.05 compared to untreated cells. **, p<0.01 compared to untreated cells as determined by unpaired t test.

BAMs 1-3 promote Ras signaling. Ras and RasGRF1, a guanidine nucleotide exchange factor involved in Ras signaling, are important intermediates in the regulation of spine density [37]. Previous work has reported that BTA-EG$_4$ could promote spine density increases in vitro in murine primary hippocampal neurons and in vivo in the hippocampus of wt mice and a 3×tg mouse model for AD [18,19]. The increase in spine density in neurons by BTA-EG$_4$ correlated with an increase in expression of RasGRF1 compared to control cells. In order to test whether the spinogenic activity induced by compounds 1-3 and BTA-EG$_6$ operated along a similar mechanistic path as BTA-EG$_4$, we analyzed the effects of these compounds on the expression level of RasGRF1 in differentiated human SH-SY5Y neuroblastoma cells. Since SH-SY5Y cells have not, to our knowledge, previously been shown to express RasGRF1, we first dosed differentiated SH-SY5Y cells with increasing concentrations of BTA-EG$_4$. Western blot analysis (FIG. 4) revealed that differentiated SH-SY5Y cells expressed detectable levels of RasGRF1 and that BTA-EG$_4$ induces a dose-dependent increase in RasGRF1 levels at similar concentrations and activity levels as was previously reported in murine primary neurons [18]. We observed a maximal increase of 20% of RasGRF1 in SH-SY5Y cells dosing with 5 μM of BTA-EG$_4$. When we exposed SH-SY5Y cells to 1 or 5 μM concentrations of compounds 1-3 or BTA-EG$_6$, we also observed increased RasGRF1 expression levels. Compounds 1, 2 and BTA-EG$_6$ at 5 μM concentrations all exhibited an approximately 20% increase in RasGRF1 expression compared to untreated cells (i.e., similar activity as BTA-EG$_4$), while dosing with 5 μM BAM3-EG$_6$ (3) led to a 70% increase in RasGRF1 expression (FIG. 4).

Effects of BAMs 1-3 on dendritic spine density. BTA-EG$_4$ was first used to assess increases in spine density in primary hippocampal neurons as a control due to its previously published ability to increase spine density [18]. After confirming an observed increase in dendritic spine density over the vehicle control (FIGS. 5A-5B), neurons were next treated with BTA-EG$_6$ and benzothiazoles 1-3. All new compounds 1-3 showed a dose-dependent increase in spine density after a 24 h exposure (FIGS. 5A-5B). In addition, compounds 1-3 were able to produce a statistically significant increase in net spine density at a lower concentration compared to BTA-EG$_6$, suggesting the structural differences (and possibly the decreased hydrophobic character) of 1-3 compared to BTA-EG$_6$ results in overall increased spinogenic activity. There was no observed change in spine density when the cells were treated with the vehicle control (0.1% DMSO) [38].

Figure 6A:
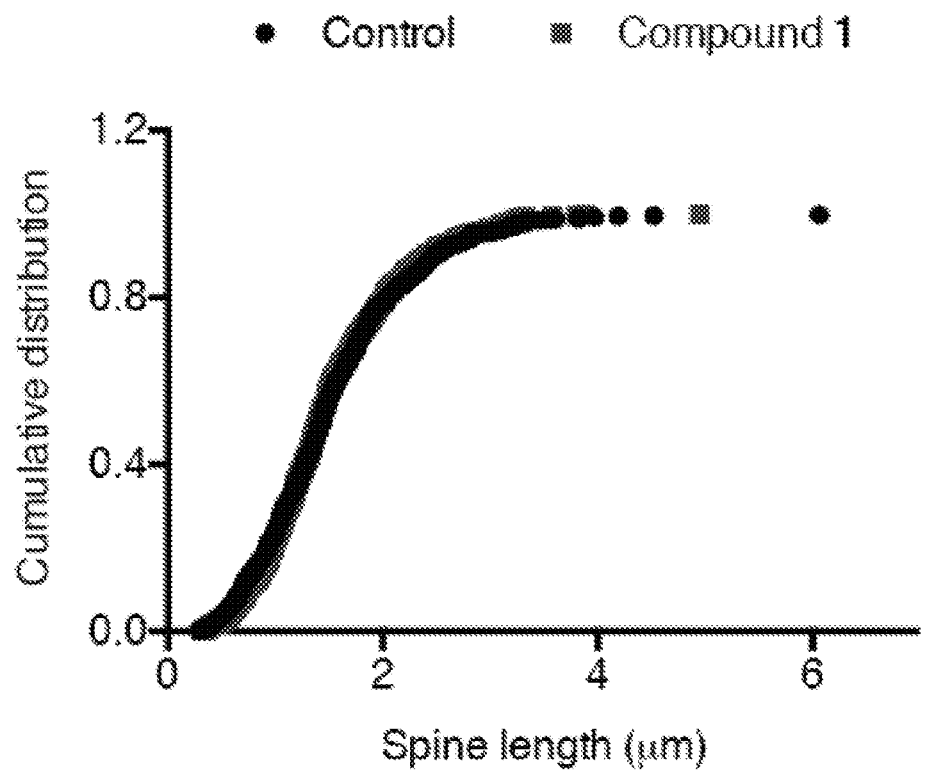
FIGS. 6A-6F. Further evaluation of the spinogenic properties of BAM1-EG$_6$ observed in rat primary hippocampal neurons. Cumulative distribution of spine length (FIG. 6A) or width (FIG. 6B) of control cells versus cells treated with compound BAM1-EG$_6$ (1 µM).
Figure 6B:
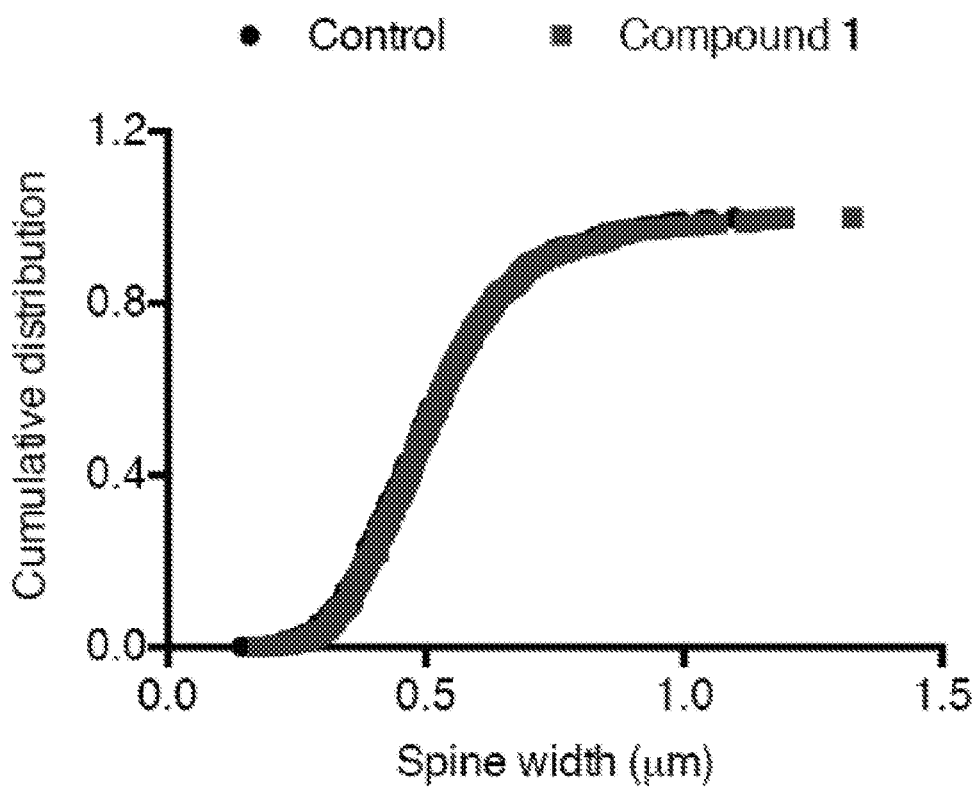

The cumulative distribution of spine length and width was also measured by taking compound 1 as a representative for this class of compounds. Importantly, no observable difference in average spine length or width was found compared to cells treated with vehicle control (FIGS. 6A-6B). This result supports that the new spines formed in presence of BAM1-EG$_6$ (1) have structurally indistinguishable morphology compared to spines that existed in the absence of BAM1-EG$_6$.

Figure 6C:
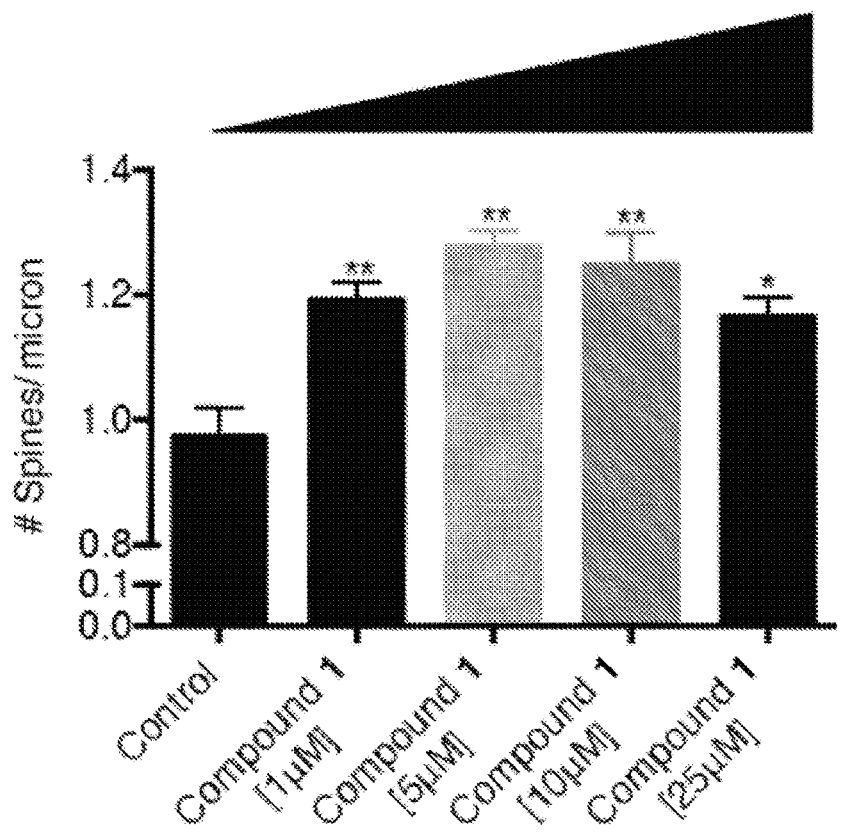

To further evaluate the spinogenic properties of the BAM agents, we used BAM1-EG$_6$ as a lead compound to investigate the extent to which the BAMs were capable of increasing dendritic spine density. Primary neurons were dosed for 24 h in the presence of 1-25 μM BAM1-EG$_6$. The maximum observed increase in spine density was ~20%, occurring with a dose of 5 μM with no further increase at higher concentrations (FIG. 6C).

Figure 6D:
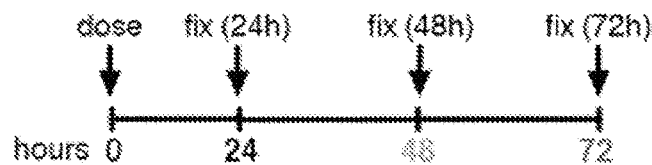
Figure 6D:
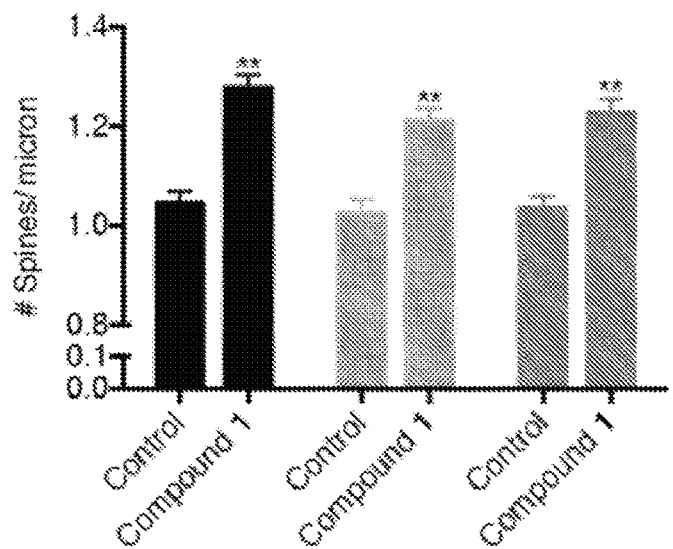

A time course of spinogenic activity was also examined in three separate experiments: In the first experiment, BAM1-EG$_6$ was exposed to primary neurons at a constant concentration (5 μM) in the culture medium for up to 72 h. At various time points, cells were fixed and spine density (as estimated by spine number per μm) was measured. This experiment revealed that the spinogenic activity of the benzothiazoles reached equilibrium within 24 h (FIG. 6D). The increase of ~20% in spine density levels (compared to treatment with vehicle) persisted for up to 3 days upon exposure to a constant concentration of the BAM1-EG$_6$.

Figure 6E:
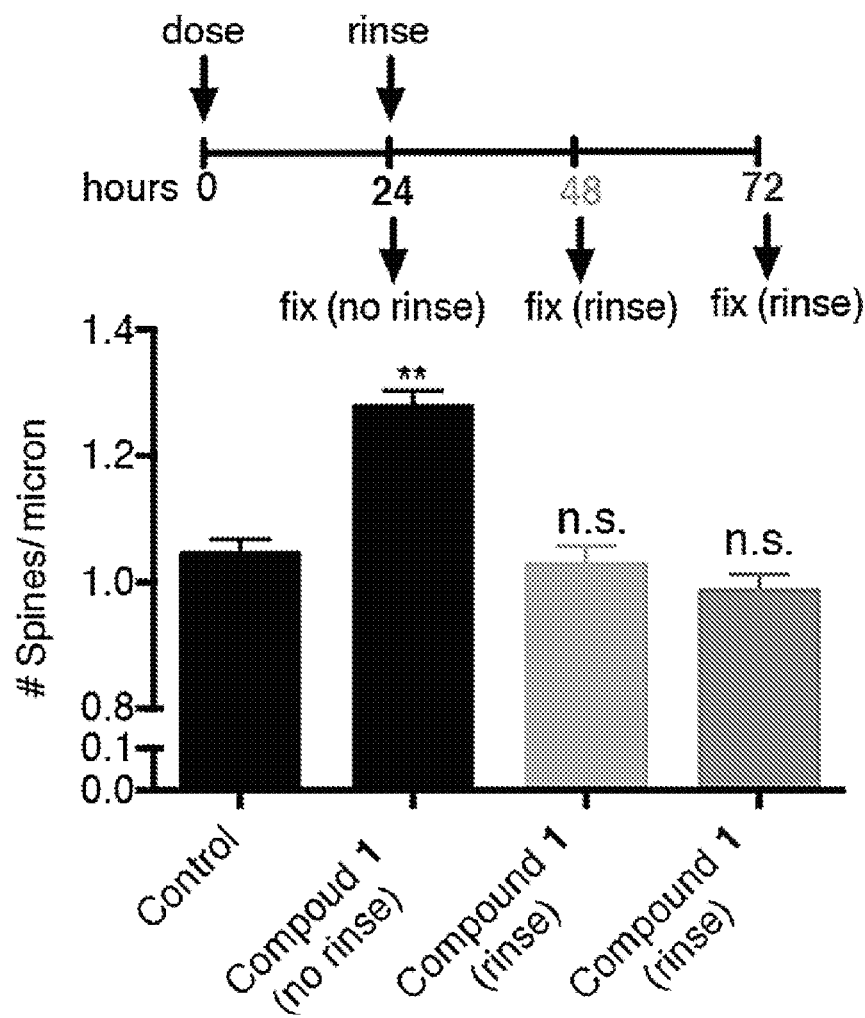

In a second experiment, we evaluated whether the spine density increases induced by the benzothiazoles persisted after the compounds have been removed from the culture medium. Primary hippocampal neurons were dosed for 24 h with 5 μM BAM1-EG$_6$, resulting in the expected ~20% increase in spine density levels compared to treatment with vehicle (0.1% DMSO). The cells were then rinsed and the culture medium was replaced with compound-free media, and the average spine density on the cells was monitored over an additional 48 h. The initial spine increase after 24 h exposure to BAM1-EG$_6$ did not persist once the compound was removed, with the density of spines returning back to normal levels (i.e., to the spine density observed in control cells) within 24 h of removal of BAM1-EG$_6$ (FIG. 6E).

Figure 6F:
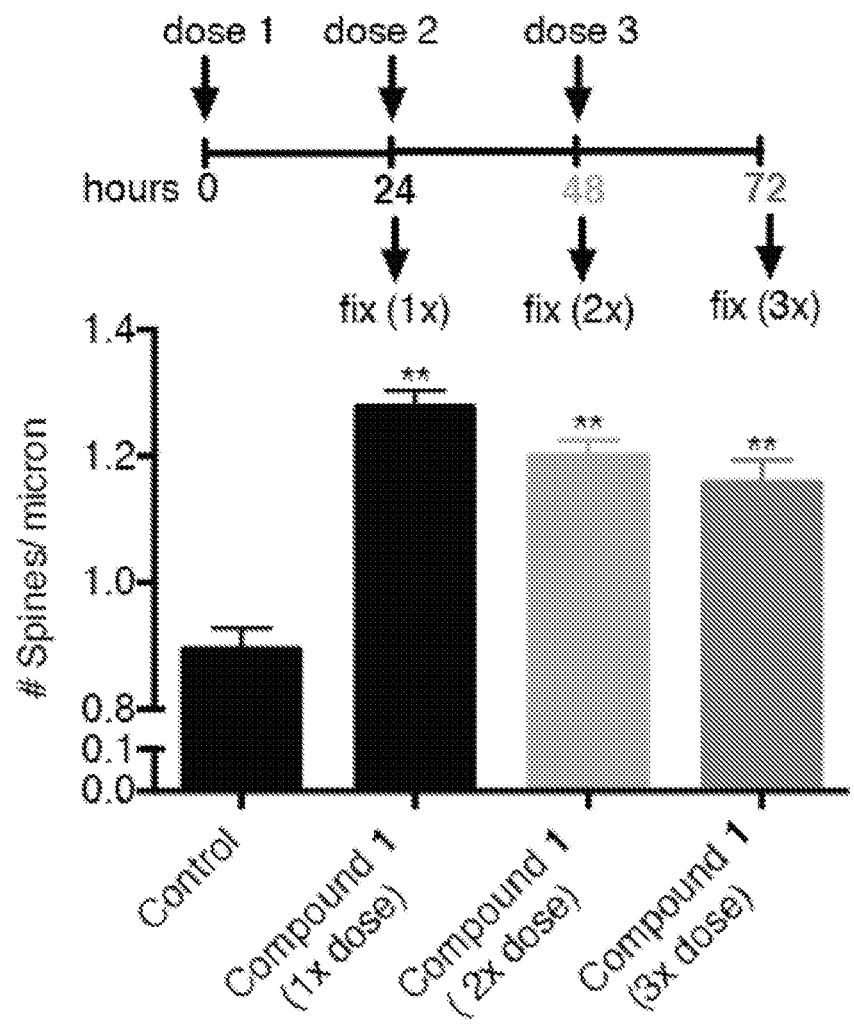

In a third experiment, we monitored the effect on spine density in primary neurons by adding fresh aliquots of BAM1-EG$_6$ every 24 h to the culture medium over a 72 h period. Primary neurons were initially incubated in culture media containing a final concentration of 5 BAM1-EG$_6$ (1× dose). At 24 hours (2× dose) and 48 hours (3× dose) of incubation, an additional 2 μL of a 5 mM BAM1-EG$_6$ DMSO stock (final concentration 5 μM, 0.1% DMSO) was added to the culture medium. We found that further addition of BAM1-EG$_6$ every 24 h (which putatively increased the final concentration of compound after every addition) did not result in further increases in dendritic spine density above the original observed increase of ~20% after 24 h exposure of 5 μM BAM1-EG$_6$ (FIG. 6F).

Figure 7A:
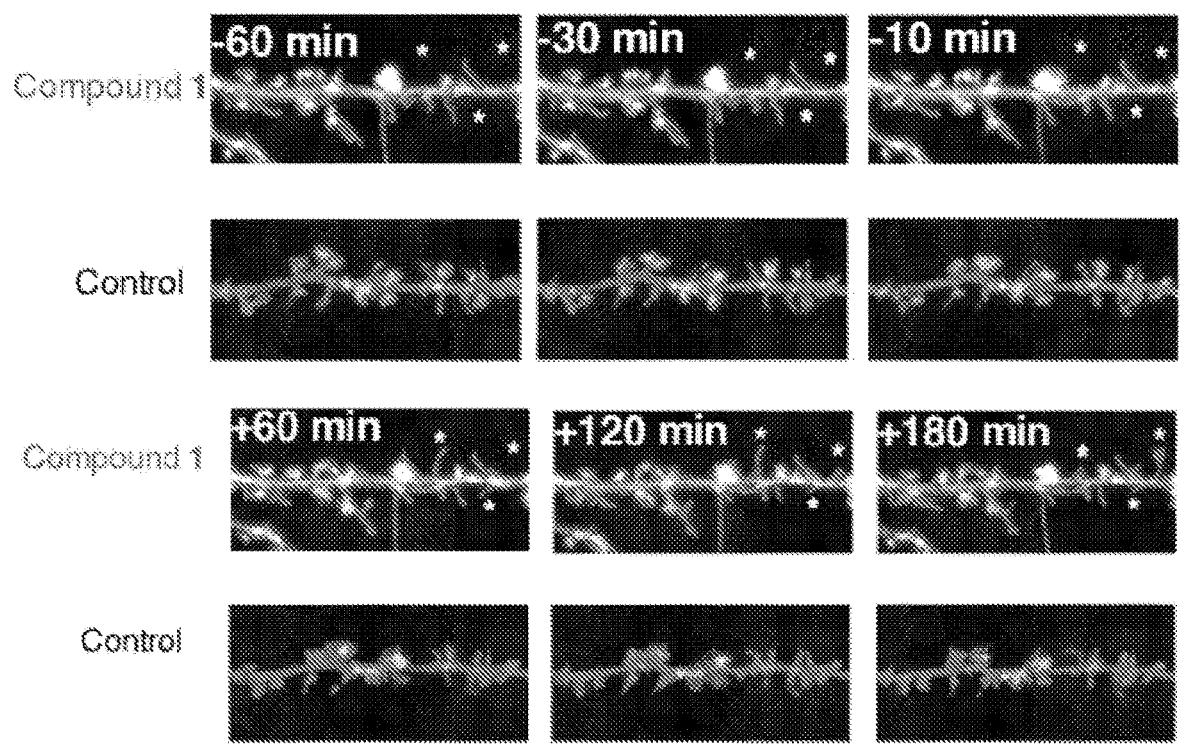
FIGS. 7A-7B. Live imaging showing the increase in formation of new spines upon dosing with BAM1-EG$_6$ (compound 1) (FIG. 7A) Representative segments (20 microns) of live cells before (−time) and after dosing (+time) with BAM1-EG$_6$ (5 µM) or vehicle control (0.1% DMSO). * denotes new spines.
Figure 7B:
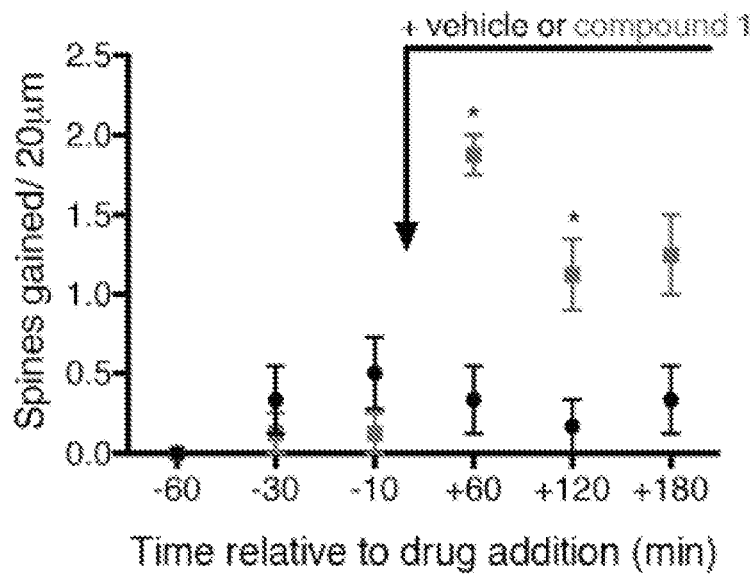
Figure 7B:
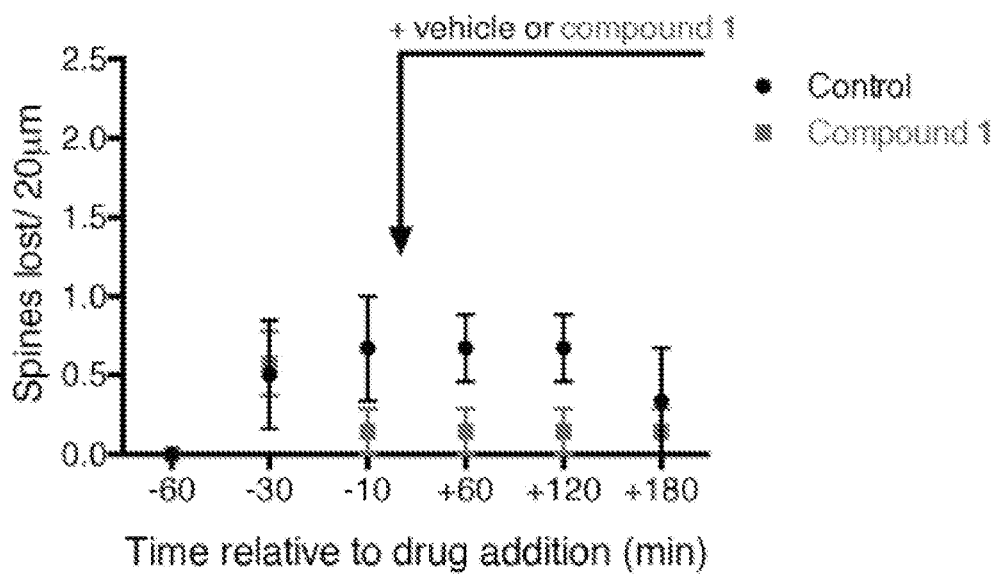

BAMs 1-3 promote the formation of new dendritic spines. An observed increase in dendritic spine density by benzothiazoles 1-3 could arise either by promoting the formation of new spines or by increasing the stability of previously formed dendritic spines. In order to help elucidate which mechanistic pathway BAMs promotes dendritic spine density alterations, we monitored the changes in spine number in real time by periodically capturing live confocal images of primary neurons over a 4 h time period. To account for baseline changes in spine dynamics, neurons were monitored 1 h prior to dosing. Live imaging then continued up to 3 h after dosing with either compound 1 (5 μM) or the vehicle control to gain insight into the spine changes induced by compound 1. We were able to observe that dosing with compound 1 lead to a statistical increase in new spines compared to the control 60 min after dosing, while no significant change in spine loss was observed over the same time period (FIGS. 7A-7B).

Figure 8A:
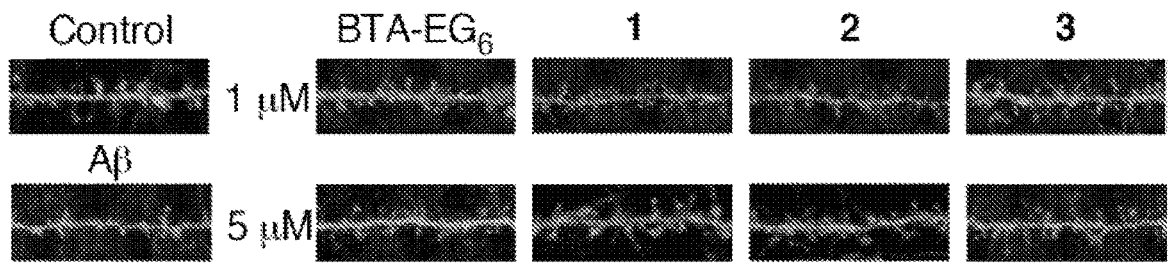
FIGS. 8A-8B. Compounds counteract Aβ associated net spine loss in rat primary hippocampal neurons.
Figure 8B:
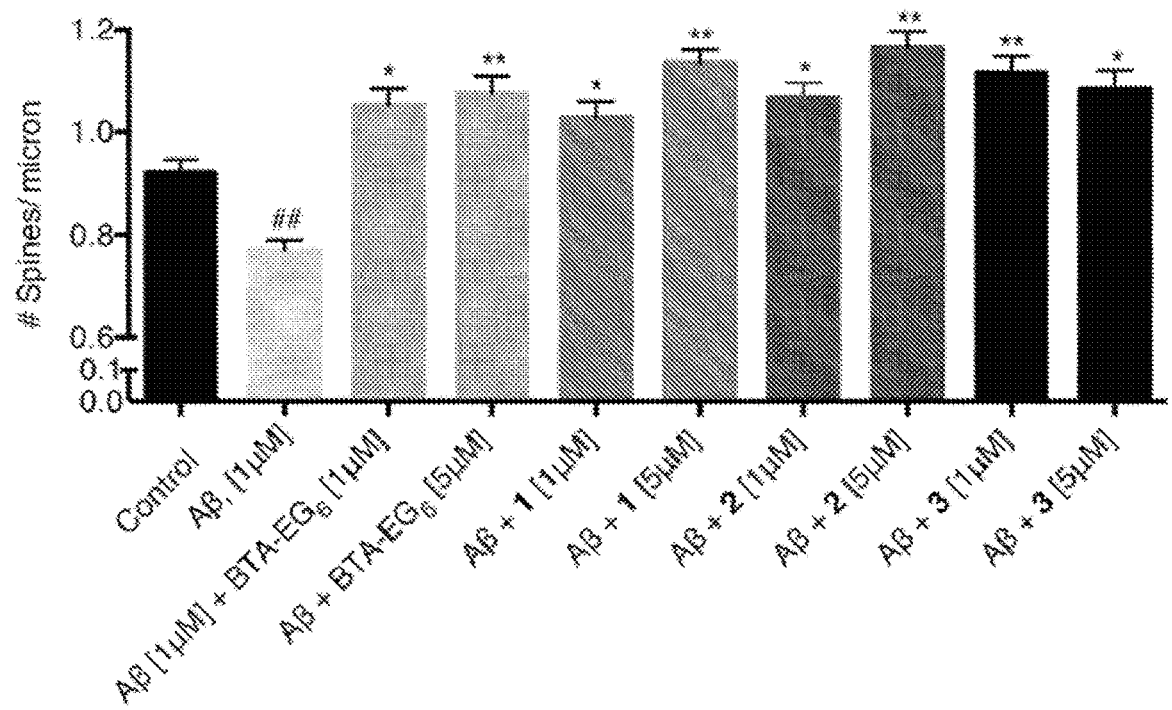

BAMs 1-3 rescue Aβ-induced spine loss. Since BAMs 1-3 were able to increase dendritic spine density in primary hippocampal neurons (FIGS. 5A-5B), we examined if these new compounds could alleviate spine loss observed in neurons exposed to aggregated amyloid-β (Aβ 1-42), the toxic peptide cleavage product of the amyloid precursor protein (APP) associated with AD. We treated primary neurons for 3 days with media containing aggregated Aβ (1-42) with and without the presence of BAMs 1-3 or BTA-EG$_6$. We observed around a 20% decrease in spine density in primary neurons that were incubated in the presence of 1 μM aggregated Aβ (1-42) alone for 3 days (FIGS. 8A-8B). In contrast, when we treated primary neurons with 1 μM Aβ (1-42) and 1 or 5 μM concentrations of BAMs 1-3 or BTA-EG$_6$, we observed a net increase in dendritic spine density by ~20% compared to control (FIGS. 8A-8B). Furthermore, the observed net increase in spine density in cells treated simultaneously with Aβ (1-42) and BAMs 1-3 or BTA-EG$_6$ were ~50% higher than in cells treated with Aβ (1-42) alone. These results demonstrate that BTA-EG$_6$ and benzothiazoles 1-3 are capable of counteracting the net decrease in dendritic spine density induced by aggregated Aβ (1-42) peptides.

Many cognitive disorders are accompanied with loss of dendritic spines, yet there are few examples of molecules that promote the formation of new dendritic spines. The capability to promote increases in spine density through external administration of a drug could lead to a better understanding of the underlying circuitry affecting cognitive behavior, and, ultimately, to novel approaches for treatment of cognitive disorders.

We previously reported that oligo(ethylene glycol) derivatives of benzothiazole could insert into planar lipid bilayers and induce membrane lysis [23]. The concentration required to observe lysis in membranes roughly correlated with the observed cytotoxicity of the compounds in human SH-SY5Y neuroblastoma cells (IC$_{50}$~60 μM), suggesting lysis of cells as the significant factor for the apparent toxicity [39] of the BTA-EG$_x$ compounds at high micromolar concentrations [23]. Hence, we hypothesized that altering the hydrophobic core of these molecules would decrease their energetic driving force to partition into membranes, thereby reducing their toxicity.

With a goal of generating structural analogs of BTA-EG$_6$ with reduced hydrophobic character, we designed and synthesized benzothiazole analogs 1-3 (FIGS. 1 and 2). This new set of benzothiazoles exhibited low overall toxicity (FIGS. 3A-3B) compared to parent BTA-EG$_6$. Interestingly, we did not find a correlation between the calculated log P values (a typical measure of hydrophobicity) and toxicity. Instead, we found a positive correlation between solvent-accessible surface area (SASA) and toxicity in BTA-EG$_6$ and all of its derivatives. The SASA could, therefore, represent a more useful and quantifiable alternative parameter to Log P for guiding the development of additional members of this class of spinogenic compounds with low toxicity.

While reducing toxicity of benzothiazole agents is an important step towards improving their biocompatibility, it is also important to assess whether the new BAMs 1-3 retain the potential beneficial biological activity of the parent compound. The capability of BTA-EG$_4$ to promote an increase in dendritic spine density is a distinctive and extremely rare property for any small molecule reported to date. The results demonstrate that the new benzothiazoles 1-3 are indeed capable of promoting dose-dependent increases in dendritic spine density in primary hippocampal neurons (FIGS. 5A-5B), with maximal spine density increases of ~20% within 24 hours of exposure to cells. This result contrasts previously reported studies on the spinogenic activity of 17β-estradiol, which required 96 hours to induce maximal increase in spine density levels in primary hippocampal neurons compared to control cells [40]. These contrasting observations suggest that BAM agents and 17β-estradiol promote spine density increases by different molecular mechanisms.

The analysis of the cumulative distribution of spine width and length of cells exposed to BAM1-EG$_6$ showed no difference compared to control cells (FIGS. 6A-6B), demonstrating that the increase in spine density by BAMs does not affect the overall distribution of spine morphology in the cells [41]. Temporal studies showed that the spine density increase in neurons stably persisted for 72 h in the presence of BAM1-EG$_6$, while the spine density levels returned to basal levels within 24 h of removal of this compound (FIGS. 6D-6E). This capability of BAM agents to reversibly control the magnitude of spine density changes in primary neurons may be very attractive as a tool for further studies on the relationship between dendritic spines and other parameters related to neural circuitry.

Live cell imaging and biochemical studies support that these benzothiazoles promote the formation of new dendritic spines in neurons (FIGS. 7A-7B) through a mechanism that involves Ras activation by increasing RasGRF1 expression levels (FIG. 4). Previous studies showed that shRNA knockdown of RasGRF1 in primary neurons completely blocked the effect of BTA-EG$_4$ on spine density increases [18], further supporting the involvement of Ras signaling in the spinogenic activity of the BAM agents. Importantly, we showed that BAMs 1-3 and BTA-EG$_6$ were able to rescue dendritic spine loss caused by the presence of aggregated Aβ (FIGS. 8A-8B), which demonstrate that BAMs 1-3 have potential to counteract one of the earliest observed pathological events associated with AD [16,42].

In conclusion, we used rational design to develop a novel set of benzothiazole amphiphiles 1-3 with improved biocompatibility compared to the previously reported BTA-EG$_x$ compounds [17-19]. These new compounds were capable of 1) promoting dose-dependent increases in dendritic spine density, 2) temporally and reversibly controlling elevated spine levels, and 3) counteracting Aβ-induced dendritic spine loss. Current efforts are focused on identification of the cellular target for the BAM agents and additional mechanistic details leading to the spinogenic activity of these compounds. These novel benzothiazoles represent a significant step towards the development of new tools to study and treat spine related disorders, and may also lead to a new class of general cognitive enhancers.

Materials. Synthetic Aβ(1-42) peptide was purchased from PL Lab. SH-SY5Y human neuroblastoma cells (Product No: CRL-2266) and 3-(4,5-dimethylthiazolyl-2)-2, 5-diphenyltetrazolium bromide (MTT) cell proliferation assay (Product No: 30-1010K) were purchased from American Type Culture Collection (ATCC) (Manassas, Va.). Antibodies used for western blots were mouse anti-RasGRF1 (BD 610149), mouse anti-tubulin-β (Thermo MS-1226-P) and a TRITC labeled goat anti-mouse antibody (JAX 115-025-003). All chemical reagents were purchased and used as is from Sigma Aldrich or Fisher unless otherwise stated.

Compounds. BTA-EG$_6$ and BTA-EG$_4$ were synthesized as previously reported [25]. The general synthetic procedures we used to prepare benzothiazole amphiphiles (BAMs 1-3) are outlined in FIG. 2. For the synthesis of the benzothiazole core for BAM2, commercially available 4-hydroxy benzaldehyde (4) was alkylated with and 2-chloro-N-methylacetamide (5) via an in situ Finklestein reaction [26]. The aryl ether (6) underwent a rearrangement under basic conditions to yield 4-N-(methylamino) benzaldehyde (7) [27]. Microwave irradiation in ionic liquid ([pmIm]Br) [28] of 2-aminothiophenol (8) with benzaldehyde (7) afforded benzothiazole 9. An analogous microwave-assisted reaction [29] between 8 and 12 gave 2-(4-(methylthio)phenyl)benzo[d]thiazole (13) in good yield. The methylthiol group on 13 was then oxidized to the sulfoxide via mCPBA oxidation to yield 2-(4-(methylsulfinyl)phenyl) benzo[d]thiazole (14). Pummerer rearrangement [30,31] of compound 16 gave the α-acyloxy-thioether (16), which was converted to the thiol (17). Compounds 9, 10 (commercially available), and 16 were then reacted with EG$_6$-Iodide (11) [23] under standard nucleophilic substitution conditions to yield BAM1-EG$_6$ (1), BAM2-EG$_6$ (2), and BAM3-EG$_6$ (3), respectively.

Alkylation of 4-hydroxy benzaldehyde (6). 4-Hydroxy benzaldehyde 4 (2 g, 16.5 mmole, 1.1 equiv.) and anhydrous potassium carbonate (K$_2$CO$_3$) (4.14 g, 29.9 mmole, 2 equiv.) were dissolved in acetone (30 mL) and let stir under nitrogen (N$_2$) for 30 min. Then 2-chloro-N-methylacetamide 5 (1.61 g, 15 mmole, 1 equiv.) and potassium iodide (KI) (249 mg, 1.5 mmole, 0.1 equiv.) were added and let reflux for 24 h. After cooling to room temperature (RT), solids were filtered off and the solvent was removed and replaced with dichloromethane (DCM). Extraction was done with 10% sodium hydroxide (NaOH) followed by column chromatography purification (95% DCM/methanol (MeOH)) to yield compound 6 as a white solid (2.4 g, 83% yield). $^1$H NMR (500 MHz, CDCl$_3$): δ 9.91 (s, 1H), 7.88 (d, 2H), 7.04 (d, 2H), 6.50 (b, 1H), 4.57 (s, 2H), 2.93 (s, 3H). ESI-MS (m/z): 194.12 [M+H]$^+$ Synthesis of 4-N-(methylamino) benzaldehyde (7). To a round bottom with dry toluene, compound 6 (300 mg, 1.55 mmole, 1 equiv.) and potassium hydroxide (KOH) pellets (174 mg, 3.10 mmole, 2 equiv.) were added and let reflux for 24 h. After cooling to RT, the reaction was put on ice and water was added. The organic layer was washed 3× with water, dried, and concentrated. Column chromatography (50% ethyl acetate (EtOAc)/Hexanes) yielded compound 7 as a red solid (64 mg, 30% yield). $^1$H NMR (500 MHz, CDCl$_3$): δ 9.72 (s, 1H), 7.71 (d, 2H), 6.61 (d, 2H), 4.41 (b, 1H), 2.91 (s, 3H). ESI-MS (m/z): 136.19 [M+H]$^+$ Synthesis of Benzothiazole (9)[1a]. A microwave vial was charged with 2-aminothiophenol 7 (45 mg, 0.36 mmole. 1 equiv.), followed by 1-pentyl-3-methylimidazolium bromide ([pmIm]Br)[2a] (29 mg, 0.18 mmole, 0.5 equiv.) and then 4-(methylamino) benzaldehyde 8 (49 mg, 0.36 mmole, 1 equiv.). The mixture was irradiated under MW conditions (150° C., 4 min). The reaction mixture was extracted with ether/H$_2$O (4×). The ether was evaporated and the compound was purified by column chromatography (25% DCM/70% Hexanes/5% EtOAc), affording compound 9 as a light orange solid (55 mg, 64% yield). $^1$H NMR (500 MHz, CDCl$_3$): δ 8.02 (d, 1H), 7.96 (d, 2H), 7.84 (d, 1H), 7.44 (t, 1H), 7.32 (t, 1H), 6.66 (d, 2H), 2.92 (s, 3H). $^{13}$C NMR (400 MHz, CDCl$_3$): δ 169.05, 154.53, 151.82, 134.73, 129.32 (2C), 126.25, 124.50, 122.68, 122.53, 121.60, 112.24 (2C), 30.54. ESI-MS (m/z): 241.0 [M+H]$^+$ [1a] Ranu, B. C., and Jana, R. (2006) Ionic Liquid as Catalyst and Reaction Medium—A Simple, Efficient and Green Procedure for Knoevenagel Condensation of Aliphatic and Aromatic Carbonyl Compounds Using a Task-Specific Basic Ionic Liquid. European J. Org. Chem. 2006, 3767-3770. [2a] Namboodiri, V. V., and Varma, R. S. (2002) Solvent-Free Sonochemical Preparation of Ionic Liquids. Org. Lett. 4, 3161-3163.

General protocol for (ethylene glycol)$_6$ (EG$_6$) addition. Synthesis of 17-iodo-3,6,9,12,15-pentaoxaheptadecan-1-ol (EG$_6$-I) was prepared as previously described[3a]. A microwave vial was charged with EG$_6$-I (1 equiv.), benzothiazole aniline 9 or 10 (2 equiv.), potassium carbonate (3 equiv.) and tetrahydrofuran (THF). The mixture was irradiated under MW (125° C., 2 h). The mixture was filtered, concentrated and normal phase column chromatography (4% MeOH/EtOAc) followed by reverse phase column chromatography (3:1 MeOH/H$_2$O) yielded compound 1 (285 mg, 48% yield) or compound 2 (13 mg, 30% yield). [3a] Prangkio, P., Rao, D. K., Lance, K. D., Rubinshtein, M., Yang, J., and Mayer, M. (2011) Self-assembled, cation-selective ion channels from an oligo(ethylene glycol) derivative of benzothiazole aniline. Biochim. Biophys. Acta 1808, 2877-85.

BAM1-EG$_6$ (1). $^1$H NMR (500 MHz, CDCl$_3$): δ 7.99 (d, 1H), 7.92 (d, 2H), 7.84 (d, 1H), 7.43 (t, 1H), 7.30 (t, 1H), 6.76 (d, 2H), 4.97 (b, 1H), 3.73-3.58 (m, 22H), 3.39 (t, 2H). $^{13}$C NMR (500 MHz, CDCl$_3$): δ 168.92, 154.51, 151.38, 134.74, 129.13 (2C), 126.24, 124.54, 123.20. 122.55, 121.60, 113.28 (2C), 71.68, 69.81-69.03 (69.81, 69.59, 69.45, 69.30, 69.24, 69.23, 69.03), 68.74, 60.44, 43.86. HR/MS (ESI+): Calcd for [C$_{25}$H$_{34}$N$_2$O$_6$S+Na] 513.2030 found 513.2029 [M+Na]$^+$.

BAM2-EG$_6$ (2). $^1$H NMR (500 MHz, CDCl$_3$): δ 7.96 (d, 1H), 7.93 (d, 2H), 7.84 (d, 1H), 7.42 (t, 1H), 7.29 (t, 1H), 6.76 (d, 2H), 3.72-3.28 (m, 24H), 3.07 (s, 3H). $^{13}$C NMR (500 MHz, CDCl$_3$): δ 168.94, 154.64, 151.39, 134.74, 129.17 (2C), 126.19, 124.40, 122.49, 121.57, 121.55, 111.80 (2C), 72.76, 71.0-70.50 (71.00, 70.88, 70.85, 70.80, 70.76, 70.75, 70.71, 70.50), 68.73, 61.93, 52.29, 39.26. HR/MS (ESI-TOFMS+): Calcd for [C$_{26}$H$_{36}$N$_2$O$_6$S+Na] 527.2191 found 527.2187 [M+Na]$^+$.

2-(4-(methylthio)phenyl)benzo[d]thiazole (14). 2-amino thiophenol 8 (376 mg, 3 mmol, 1 equiv.), [pmIm]Br (400 mg, 0.5 equiv), 4-(methylthio)benzaldehyde 13 (457 mg, 3 mmol, 1 equiv.) were added respectively, into a 5 mL microwave tube with a stir bar. The reaction tube was microwaved for 4 min at 130° C. The reaction mixture was dissolved in diethyl ether and extracted with water to remove the ionic liquid solution. The diethyl ether was removed under reduced pressure and the crude solid 14 was purified by recrystallization in a 3:1 mixture of hexanes:EtOAc (547 mg, 71% yield). $^1$H NMR (400 MHz, CDCl$_3$): δ 8.05 (d, 1H), 8.01 (d, 2H), 7.90 (d, 1H), 7.49 (t, 1H), 7.38 (t, 1H), 7.33 (d, 2H), 2.55 (s, 3H). $^{13}$C NMR (300 MHz, CDCl$_3$): δ 143.00, 127.99, 126.56, 125.31, 123.23, 121.81, 15.39. ESI-MS (m/z): 258.25 [M+H]$^+$.

2-(4-(methylsulfinyl)phenyl)benzo[d]thiazole (15). 2-(4-(methylthio)phenyl) benzo[d]thiazole 14 (300 mg, 1.1 mmol) was dissolved in 6 mL of DCM. meta-chioroperoxybenzoic acid (m-CPBA) (242 mg, 1.4 mmol) was dissolved in 4 mL of DCM and added dropwise at 0° C. to the methyl sulfide 14 solution over a period of 20 min. NaHCO$_3$ (80 mg) was added and the solution was let stir. The reaction mixture was monitored by TLC analysis (100% EtOAc) until completion. The white precipitate was filtered away and the DCM was removed under reduced pressure to afford a white solid. The solid was purified by recrystallization in 100% EtOAc to give product 15 (254 mg, 80% yield). $^1$H NMR (400 MHz, CDCl$_3$): δ 8.26 (d, 2H), 8.11 (d, 1H), 7.94 (d, 1H), 7.78 (d, 2H), 7.53 (t, 1H), 7.44 (t, 1H), 2.79 (s, 3H). ESI-MS (m/z): 274.17 [M+H]$^+$, 296.10 [M+Na]$^+$ ((4-(benzo[d]thiazol-2-yl)phenyl)thio)methyl 2,2,2-trifluoroacetate (16). 2-(4-(methylsulfinyl)phenyl)benzo[d]thiazole (15) (50 mg, 0.18 mmol) was dissolved in 2 mL of freshly distilled DCM in an oven dried 50 mL round bottom. Trifluoroacetic anhydride (TFAA) (0.15 mL) was added to the reaction flask and the reaction was gently refluxed at 40° C. for 2 h under N$_2$. The solvent was removed under reduced pressure to afford the crude product 16 (72 mg, approximately quantitative conversion). The product was taken on to the next step without further purification. $^1$H NMR (500 MHz, CDCl$_3$): δ 8.07 (m, 3H), 7.92 (d, 1H), 7.58 (d, 8 Hz, 2H), 7.53 (t, 1H), 7.43 (t, 1H), 5.70 (s, 2H).

4-(benzo[d]thiazol-2-yl)benzenethiol (17). ((4-(benzo[d]thiazol-2-yl)phenyl)thio) methyl 2,2,2-trifluoroacetate (16) (72 mg, 0.19 mmol) was dissolved in 3 mL of MeOH and 0.6 mL of 1M NaOH was added to the reaction flask and refluxed under N$_2$ for 1 h. The reaction mixture was cooled and the solvent was removed under reduced pressure. 0.6 mL of 1M HCl was then added to the crude mixture and the product was extracted into EtOAc by washing the aqueous layer with 3×2 mL of EtOAc. The organic layer was washed with a saturated NaCl solution and dried over Na$_2$SO$_4$. The EtOAc was removed under reduced pressure to afford the crude product 17 (44 mg, 93% crude yield). $^1$H NMR (500 MHz, CDCl$_3$): δ 8.08 (d, 1H), 7.95 (d, 2H), 7.90 (d, 1H), 7.51 (t, 1H), 7.39 (m, 3H), 3.68 (s, 1H). ESI-MS (m/z): 244.28 [M+H]$^+$ 17-((4-(benzo[d]thiazol-2-yl)phenyl)thio)-3,6,9,12,15-pentaoxaheptadecan-1-ol (3). In an oven dried 50 mL round bottom, solid sodium hydride (NaH) (2 mg, 0.074 mmol) was added and the round bottom was tightly capped with a rubber septum. The round bottom was purged with N$_2$. The crude 4-(benzo[d]thiazol-2-yl)benzenethiol (17) (12 mg, 0.05 mmol, 1 equiv.) was dissolved in 1 mL of freshly distilled dimethylformamide (DMF) and added dropwise to the round bottom flask containing NaH. The reaction mixture was stirred for 30 min. 17-iodo-3,6,9,12,15-pentaoxaheptadecan-1-ol (EG$_6$-I, 20 mg, 0.05 mmol, 1 equiv.) was dissolved in 1 mL of freshly distilled DMF in a separate vial and added dropwise into reaction mixture. The reaction was then refluxed under N$_2$ for 12 h. The reaction mixture was cooled to RT and the solvent was removed under reduced pressure. The product was purified via silica gel flash chromatography (using a gradient of EtOAc:MeOH 0-4%) to afford the desired product 3 as a yellow oil (R$_f$=0.24, 100% EtOAc). The yellow oil product was purified once more using a reverse-phase preparatory plate (using a 3:1 mixture of MeOH:H$_2$O as eluent) to give final product 3 (11 mg, 44% yield).

BAM3-EG$_6$ (3). $^1$H NMR (500 MHz, CDCl$_3$): δ 8.04 (d, 1H), 7.99 (d, 2H), 7.89 (d, 1H), 7.48 (t, 1H), 7.41 (d, 2H), 7.37 (t, 2H), 3.74-3.70 (m, 4H), 3.64 (m, 16H), 3.60-3.58 (m, 2H), 3.20, (t, 2H). $^{13}$C NMR (500 MHz, CDCl$_3$): δ 167.42, 154.09, 140.57, 134.88, 130.83, 128.01, 127.86, 126.38, 125.18, 123.08, 121.62, 72.50, 70.64-70.30 (70.64, 70.59, 70.55, 70.53, 70.50, 70.30), 69.68, 61.74, 32.08. HR/MS: calcd for C$_{25}$H$_{33}$NO$_6$S$_2$ [M+Na] 530.1641 found [M+Na] 530.1640.

Measurement of Fluorescence Emission Spectra. The emission spectra of benzothiazoles in different environments was evaluated as previously described [23]. Briefly, BAMs 1-3 and BTA-EG$_6$ were diluted to a final concentration of 50 µM in deionized H$_2$O, pure octanol, and a liposome suspension. The liposomes were prepared from a total lipid concentration of 10 mM of DiPhyPC in water by the gentle dehydration rehydration method followed by tip sonication. 200 µL of each sample was transferred to a cuvette (Hellma® Analytics, Quartz SUPRASIL® (QS), 10 mm) and the fluorescence emission spectrum was measured in a PTI spectrofluorometer (0.5 nm step size) in water, octanol and an aqueous liposome suspension for BAMs 1-3 and BTA-EG$_6$. Maximal excitation and emission values ($\lambda_{max}$) for all compounds were as follows: BTA-EG$_6$ (Ex/Em 355/

420 nm), BAM1-EG$_6$ (Ex/Em 355/420 nm), BAM2-EG$_6$, (Ex/Em 365/428 nm), and BAM3-EG$_6$ (Ex/Em 335/398 nm). Each experiment was repeated at least three separate times and error bars denote standard deviation from the mean. Data was processed using ORIGIN® 7.0 (MicroCal Software, Inc., Northampton, Mass.).

Estimation of Log P and solvent accessible surface area (SASA). Log P values were calculated using Molinspiration Cheminformatics Software and solvent accessible surface area (SASA) values were calculated with PyMOL.

Measurement of Cell Viability in the Presence of BAMs 1-3 and BTA-EG$_6$. An MTT cell viability assay was performed as previously described [17]. Briefly, SH-SY5Y cells were plated in a 96 well plate at a density of 50,000 cells/well in 100 µL of 1:1 Eagle's Minimum Essential Medium (EMEM) and Ham's F12, supplemented with 10% Fetal Bovine Serum (FBS). Cells were allowed to adhere overnight (37° C., 5% CO$_2$) before dosing with 100 µL of various samples solutions of either BTA-EG$_6$ or BAMs 1-3 with final concentrations (0-250 Cells were exposed to these solutions for 24 h at 37° C., 5% CO$_2$. An MTT cell viability kit (ATCC, Product No: 30-1010K) was then used to determine cell viability. Briefly, 20 µL of the provided MTT reagent was added per well and cells were placed in the incubator for 3 h. The insoluble intracellular purple formazan was then dissolved by the addition of 100 µL of detergent reagent provided and let solubilize overnight at room temperature. The cell viability was determined by measuring the absorbance at 570 nm using a SPECTRAMAX® 190 microplate reader (Molecular Devices). All results are presented as percent reduction of MTT relative to untreated cells (100% viability), and all wells were blanked with absorbance values from the wells containing media, MTT reagent and detergent only.

Evaluation of the Cellular Internalization of BAMs 1-3 and BTA-EG$_6$. Differentiated SH-SY5Y neuroblastoma cells were plated in DMEM without phenol red (supplemented with 10% FBS and 4 mM L-glutamine) on 35 mm glass bottom dishes (MatTek) and incubated overnight. The growth media was removed and solutions of compounds in media were added to cells and allowed to incubate for 12 h before imaging. The cells were washed with Hank's balanced saline solution (HBSS) (3×) immediately before imaging. All Images were acquired on a Yokogawa spinning disk system (Yokagawa, Japan) built around an Axio Observer Z1motorized inverted microscope (Carl Zeiss Microscopy GmbH, Germany) with a 40×, 1.40 NA oil immersion objective. An Evolve 512×512 EMCCD camera (Photometrics, Canada) was used with ZEN imaging software (Carl Zeiss Microscopy GmbH, Germany). Environmental conditions were maintained at 37° C., 5% CO$_2$ with a heated enclosure and CO$_2$ controller (Pecon, Germany). Fluorescent images were captured using a 405 nm, 50 mw DPSS excitation laser and monitoring emission at 450 nm (bp 50 nm).

Western Blot Analysis of Ras-GRF1 Expression in SH-SY5Y Cells Exposed to BAMs 1-3 or BTA-EG$_6$. Differentiation of SH-SY5Y cells was performed according to a previously described procedure [32]. Briefly, cells were differentiated for 8 days by the addition of 10 µM all-trans-retinoic acid (RA) in the cell culture medium (1:1 EMEM and Ham's F12 supplemented with 10% FBS). Media with RA was changed every 2 days. After 8 days, the media was removed and new, RA-free media containing the sample solutions was added. Cells were exposed to solutions containing a final concentration of the BTA-E$_6$ and BAMs (0, 1, or 5 µM) for 24 hours at 37° C. Cells were than lysed with NP-40 buffer with protease inhibitor (Roche, ref #05892791001) and protein concentration was determined by BCA assay (Pierce BCA Assay Kit, #23225). Proteins were separated by SDS-PAGE (NUPAGE® 4-12% Bis-Tris gel, NUPAGE® MES SDS running buffer) followed by transfer onto nitrocellulose membrane (NOVEX®, LC2000). Membranes were blocked with 3% BSA in Tris-Buffered Saline with Tween 20 (TBST) for 1 h followed by incubation with primary antibodies in 3% BSA/TBST [mouse anti-RasGRF1 (BD 610149) and mouse anti-tubulin-β (Thermo MS1226-P)] overnight at 4° C. with shaking. Membranes were then washed with TBST (3×10 min) and then incubated with a TRITC labeled goat anti-mouse antibody (JAX 115-025-003) for 1 h at RT with shaking. After 1 h, the membranes were washed with TBST (6×5 min) and the proteins were visualized using a Typhoon 8600 variable mode imager (GE Healthcare). The density of each band was then quantified using ImageJ software as a percentage of control following normalization to β-tubulin.

Neuronal Cultures. Rat dissociated hippocampal neurons from postnatal day 1 were plated at a density of 45,000 cells/cm$^2$ onto poly-D-lysine-coated coverslips. Neurons were maintained in B27 supplemented Neurobasal media (Invitrogen) until days in vitro (DIV) 18-23 as previously described [33,34].

Neuronal Treatments. For all neuronal treatments the following general protocol was followed: Briefly, 18-23 DIV rat dissociated hippocampal neurons were dosed with various concentrations (0-50 µM final concentration) of BAMs 1-3 or BTA-EG$_x$ (with 0.1% final DMSO concentration) for various times (24-72 h depending on the experiment). After dosing and at the desired time point, the media was removed and cells were rinsed with PBS-MC (phosphate-buffered saline, 1 mM MgCl$_2$ and 0.1 mM CaCl$_2$). Following rinsing, cells were fixed with 4% paraformaldehyde (PFA)/sucrose in PBS for 10 min at RT. After fixation, coverslips were carefully rinsed (3×PBS-MC) and then mounted onto slides (Polysciences Inc., 18606) for imaging.

Sindbis Production. PalGFP SinRep5 DNA was obtained [35]. Recombinant Sindbis virion production was accomplished through RNA transcription using the SP6 mMessage MMACHINE® kit (Ambion, Austin, Tex.). Electroporation of RNA into baby hamster kidney cells (BHK) was completed using a BTX ECM 600 electroporator (BTX, Holliston, Mass.) at 220V, 129Ω, and 1050 µF. After 24 h, virion was collected and concentrated by centrifugation at 20,000 rpm for 90 min using a Beckman Coulter Optima MAX Ultracentrifuge (Beckman Coulter, Indianapolis, Ind.). The treated neurons were infected with palGFP expressing sindbis 18 h prior to fixation.

Confocal Microscopy and Dendritic Spine Analysis. For all imaging of neurons, we used a Leica DMI6000 inverted microscope outfitted with a Yokogawa Spinning disk confocal head, an Orca ER High Resolution CCD camera (6.45 µm/pixel at 1×) (Hamamatsu), Plan Apochromat 63×/1.4 na objective, and PerkinElmer solid-state laser with 488 nm excitation. Confocal z-stacks were acquired in all experiments and all imaging was acquired in the dynamic range of 8-bit acquisition (0-255 pixel intensity units, respectively) with Volocity (PerkinElmer) imaging software. Imaged dendrites were straightened using ImageJ, and spine density was the number of manually counted spines divided by dendrite segment length. The analyzer was blind to treatment and statistical significance was determined between experimental conditions by either unpaired t tests (two groups) or by ANOVA and indicated post hoc multiple-comparison test (>2 experimental conditions).

Real Time Imaging of Spine Changes in Rat Primary Hippocampal Neurons. For this study, 21 DIV neurons plated in 35 mm dishes (MatTek) were rinsed 3× with an excess of HBSS and then left in HBSS for the duration of imaging. For live imaging we kept cells at 37° C. and used a Leica DMI6000 inverted microscope outfitted with a Yokogawa Spinning disk confocal head, an Orca ER High Resolution CCD camera (6.45 µm/pixel at 1×) (Hamamatsu), Plan Apochromat 63×/1.4 na objective, and PerkinElmer solid-state laser with 488 nm excitation. The spine changes on the same neuron were monitored 1 h before dosing (−60 min) and up to 3 h after dosing (+180 min). Dosing occurred at t=0 and consisted of either 0 (for control) or 5 µM BAM1-EG$_6$. Overall neuron health was monitored before and after each imaging session and only healthy neurons were analyzed. For each condition, neurons from three different neuronal preparations (prep) were used and two neurons per prep were monitored. Confocal z-stacks were acquired in all experiments and all imaging was acquired in the dynamic range of 8-bit acquisition (0-255 pixel intensity units, respectively) with Volocity (PerkinElmer) imaging software. For analysis, imaged dendrites were straightened using ImageJ and the same dendrite length was analyzed for each condition. Spines gained were counted as any new spines found at each respective time point and spines lost were counted as spines that disappeared from the analyzed segment. The analyzer was blind to treatment.

Preparation and Characterization of Aggregated Aβ(1-42). Aggregated Aβ(1-42) was prepared as previously described [36]. Briefly, Aβ(1-42) was initially solubilized in 100% 1,1,1,3,3,3,-hexafluoro-2-propanal (HFIP) to 1 mM concentration at RT for 21 h with shaking. The solution was sonicated and vortexed before it was diluted in cold nanopure water (2:1 H$_2$O:HFIP). Aliquoted fractions were lyophilized for 2 days, followed by storage at −80° C. until use. Solutions of Aβ were obtained by dissolving Aβ in sterile PBS to a concentration of 100 µM and incubated at 37° C. for 3 days before use. Western blot analysis of the three day incubated Aβ was carried out to determine composition. Briefly, proteins were separated using a 12% Tris-Bis gel (NUPAGE® NOVEX®) followed by transfer to nitrocellulose membrane (NOVEX®, LC2000) (1 h, RT). Membranes were blocked with 5% Milk/TB ST (45 min, RT, with shaking) and then incubated with a mouse monoclonal antibody (6E10) overnight (4° C., with shaking). Following primary antibody incubation, membranes were washed with TBST (3×10 min), and then incubated with an ECL™ Horseradish Peroxidase linked Anti-mouse secondary (GE, #NA931V). After washing the membrane (6×5 min/TBST) the detection of monomeric, oligomeric, and fibrillary Aβ was carried out using an AMERSHAM™ ECL™ Prime Western Blotting Detection Reagent (GE Healthcare) followed by detection on film (Freedom Imaging, SRX-101A). The gel was quantified using FIJI and percentage of each composition was calculated by dividing the intensity of each aggregation state over the total intensity for Aβ in the lane. This preparation of Aβ lead to a composition of ~12% monomers, ~16% low MW oligomers, and ~72% mixture of soluble protofibrils/fibrils. Aggregated Aβ was also characterized by EM, MALDI-TOF, and binding by Thioflavin T.

Rescue of Aβ-Induced Spine Loss in Rat Primary Hippocampal Neurons. We followed the same general dosing procedure as described for neuronal treatment, except with the following changes: Briefly, 18 DIV rat dissociated hippocampal neurons were dosed with a final concentration of 1 µM of aggregated Aβ(1-42) with or without the presence of 1 or 5 µM of BAMs 1-3 or BTA-EG$_6$ for 3 days. Control cells were treated with vehicle control only (0.1% DMSO) for the three-day period. After dosing, media was removed, cells were rinsed with PBS-MC and then fixed with 4% paraformaldehyde (PFA)/sucrose in PBS for 10 min at RT. After fixation, coverslips were carefully rinsed (3×PBS-MC) and then mounted onto slides (Polysciences Inc., 18606) for imaging. All analysis was done blinded and at least 7 neurons per coverslip were analyzed and each experiment was repeated at least three separate times from neurons from three different preparations.

B. Induction of Spine Formation in Human

Figure 9:
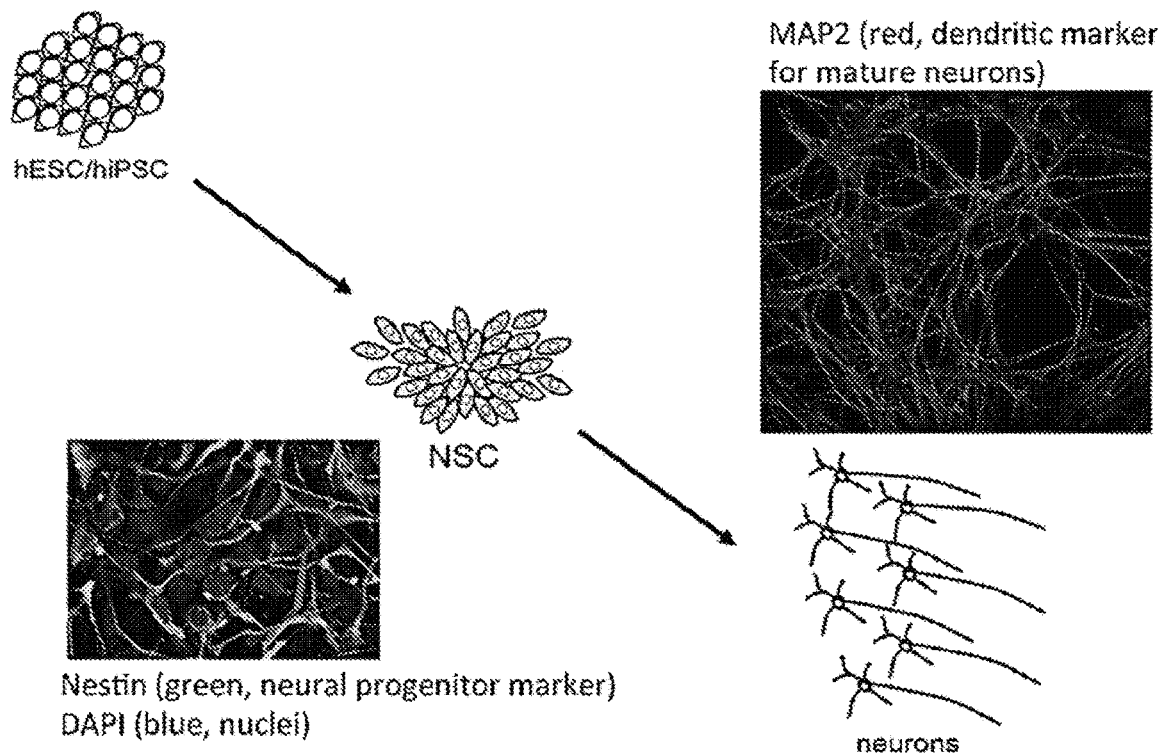
FIG. 9. The figure depicts the progression of hESC/hiPSC (human embryonic stem cells/human induced pluripotent stems cells) to NSC (neural stems cells) and eventually to neurons. The intermediate filament protein nestin (lower left micrograph) is a widely employed marker of multipotent neural stem cells. DAPI (2-(4-amidinophenyl)-1H-indole-6-carboxamidine) is a fluorescent stain that binds strongly to A-T rich regions of DNA. MAP2 (microtubule-associated protein 2) is a marker for neuronal differentiation. See micrograph in upper right.

FIG. 9 depicts the progression of hESC/hiPSC (human embryonic stem cells/human induced pluripotent stems cells) to NSC (neural stems cells) and eventually to neurons.

Figure 10:
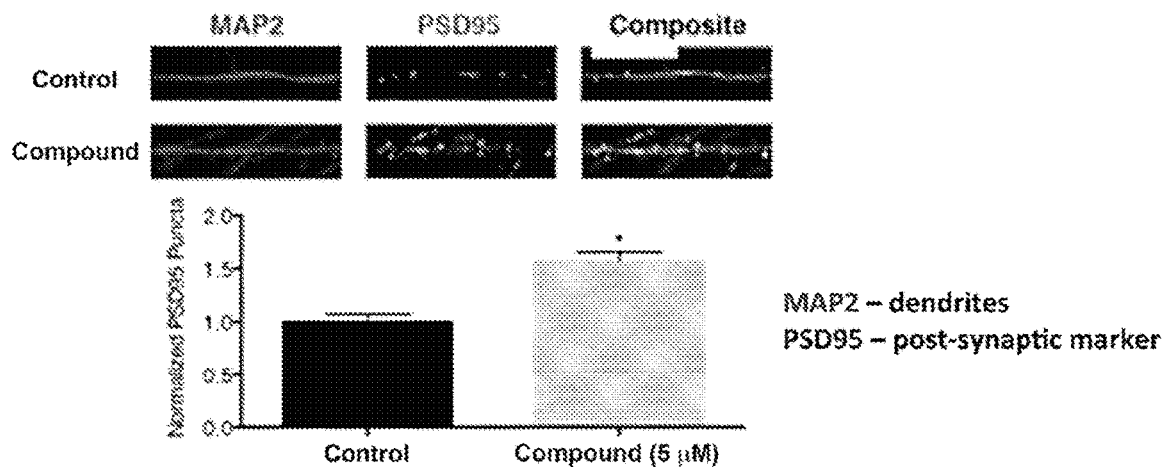
FIG. 10. Quantification of spine density of PSD95 puncta from 3-month differentiated NSC treated with compound or vehicle control The figure depicts neuron micrographs with staining for MAP2, PSD95 and composite under control and compound administration conditions. "Compound" refers to BAM3-EG$_6$ (5 µM), as depicted in FIG. 1. "Control" refers to DMSO (0.1%). MAP2 is a marker for dendrites, and PSD95 is a marker for post-synaptic features. A histogram (below) depicts normalized PSD95 puncta under control and compound administration conditions. It is observed that BTA-EG$_4$ increases spine density by about 50% compared to control in human iPSC-derived neurons.

FIG. 10 depicts quantification of spine density of PSD95 puncta from 3-month differentiated NSC treated with compound or vehicle control. It is observed that BTA-EG$_4$ analog (e.g., those depicted in FIG. 1) increases spine density by about 50% compared to control in human iPSC-derived neurons.

C. Identification of Cellular Targets for BTA-EG$_4$.

Figure 11:
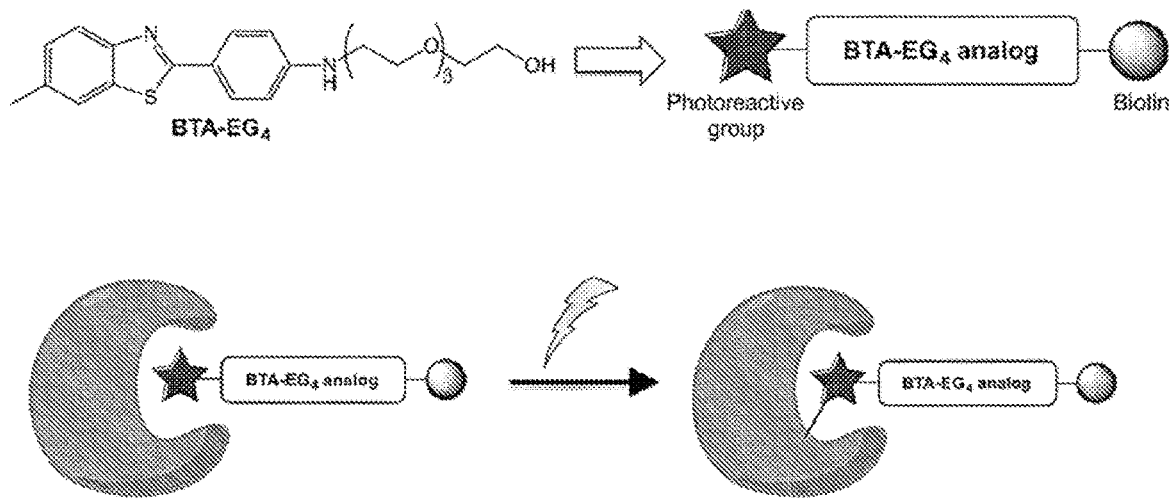
FIG. 11. The figure depicts a schematic of a BTA-EG$_4$ photoaffinity labeling procedure, useful for identification of cellular targets. The "BTA-EG$_4$" analog refers to the BAM analogs, such as the compounds depicted in FIG. 1
Figure 12:
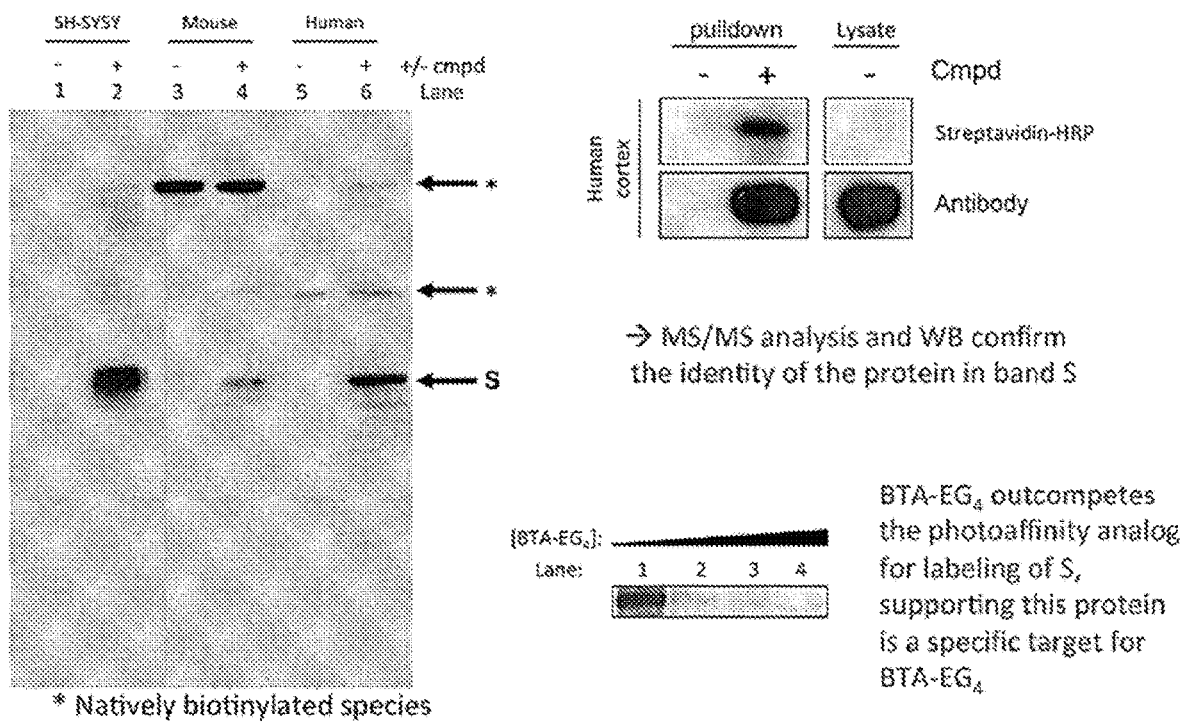
FIG. 12. The figure depicts (left panel) photoaffinity pulldown assays in human neuroblastoma cells (SH-SYSY), midbrain tissue from APP/PS1 mice (i.e., a mouse model for Alzheimer's disease), and adult human cortex. Band S refers to a band of proteins that include the protein fascin.

FIG. 11 depicts a schematic of a BTA-EG$_4$ photoaffinity labeling procedure, useful for identification of cellular targets. FIG. 12 depicts (left panel) photoaffinity pulldown assays in human neuroblastoma cells (SH-SYSY), midbrain tissue from APP/PS1 mice (i.e., a mouse model for Alzheimer's disease), and adult human cortex. It is observed that BTA-EG$_4$ analogs outcompete the photoaffinity analog for labeling of protein S, wherein protein band 'S' includes fascin, (left panel), supporting that this protein is a specific target for BTA-EG$_4$ and analogs thereof (e.g., BAM analogs depicted in FIG. 1 and the compounds of formula I)

D. Demonstration that BTA-EG4 Analogs are Anti-Metastatic/Anti-Migration Cancer Agents.

Figure 13:
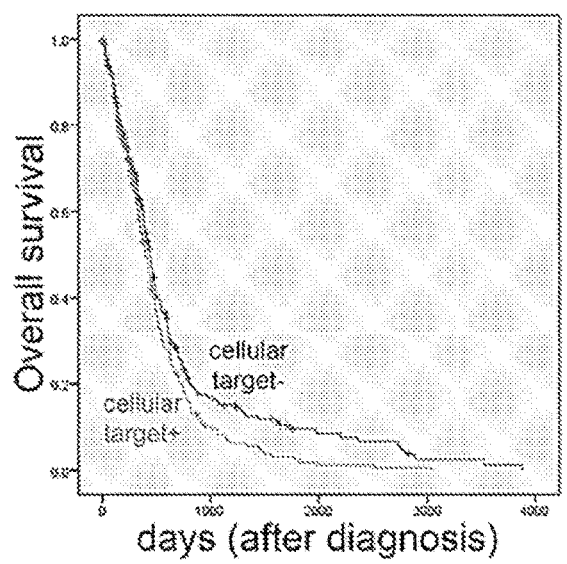
FIG. 13. The figure depicts demonstration of BTA-EG4 analogs (i.e. BAM analogs depicted in FIG. 1) useful as anti-metastatic/anti-migration cancer agents. Left graph: Overall survival over time after diagnosis, demonstrating that higher expression of protein target in brain cancer (glioblastoma) patients (N=521) correlates with overall lower survival. Right histogram: Histogram demonstrates that BTA-EG4 analogs exhibit anti-migration activity in human glioblastoma cells in a Boyden-chamber cell migration assay.
Figure 13:
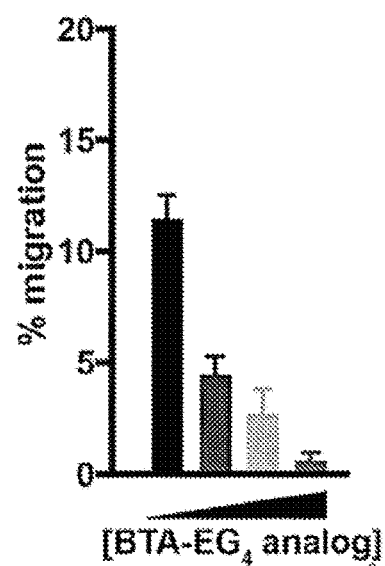

FIG. 13. depicts that BTA-EG4 analogs (e.g., BAM analogs depicted in FIG. 1) are useful as anti-metastatic/anti-migration cancer agents. Left graph: Overall survival over time after diagnosis, demonstrating that higher expression of protein target in brain cancer (glioblastoma) patients (N=521) correlates with overall lower survival. Right histogram: Histogram demonstrates that BTA-EG4 analogs (e.g., BAM analogs depicted in FIG. 1 and the compounds of formula I) exhibit anti-migration activity in human glioblastoma cells in a Boyden-chamber cell migration assay.

REFERENCES AND FOOTNOTES

[1] Nimchinsky, E. A., Sabatini, B. L., and Svoboda, K. (2002) Structure and function of dendritic spines. Annu. Rev. Physiol. 64, 313-53; [2] Matsuzaki, M., Honkura, N., Ellis-Davies, G. C. R., and Kasai, H. (2004) Structural basis of long-term potentiation in single dendritic spines. Nature 429, 761-6; [3] Kasai, H., Matsuzaki, M., Noguchi, J., Yasumatsu, N., and Nakahara, H. (2003) Structure-stability-function relationships of dendritic spines. Trends Neurosci. 26, 360-8; [4] Bourne, J. N., and Harris, K. M. (2008) Balancing structure and function at hippocampal dendritic spines. Annu. Rev. Neurosci. 31, 47-67; [5] Moser, M. B., Trommald, M., and Andersen, P. (1994) An increase in dendritic spine density on hippocampal CA1 pyramidal cells following spatial learning in adult rats suggests the formation of new synapses. Proc. Natl. Acad. Sci. U.S.A 91, 12673-5; [6] Penzes, P., Cahill, M. E., Jones, K. A., VanLeeuwen, J.-E., and Woolfrey, K. M. (2011) Dendritic spine pathology in neuropsychiatric disorders. Nat. Neurosci. 14, 285-93; [7] Lai, K.-O., and Ip, N. Y. (2013) Structural plasticity of dendritic spines: the underlying mechanisms and its dysregulation in brain disorders. Biochim. Biophys. Acta 1832, 2257-63; [8] Fiala, J. C., Spacek, J., and Harris, K. M. (2002) Dendritic Spine Pathology: Cause or Consequence of Neurological Disorders? Brain Res. Rev. 39, 29-54; [9] Schulz-Schaeffer, W. J. (2010) The synaptic pathology of alpha-synuclein aggregation in dementia with Lewy bodies, Parkinson's disease and Parkinson's disease dementia. Acta Neuropathol. 120, 131-43; [10] van Spronsen, M., and Hoogenraad, C. C. (2010) Synapse pathology in psychiatric and neurologic disease. Curr. Neurol. Neurosci. Rep. 10, 207-14; [11] Kolomeets, N. S., Orlovskaya, D. D., Rachmanova, V. I., and Uranova, N. A. (2005) Ultrastructural alterations in hippocampal mossy fiber synapses in schizophrenia: a postmortem morphometric study. Synapse 57, 47-55; [12] Glantz, L. A., and Lewis, D. A. (2000) Decreased Dendritic Spine Density on Prefrontal Cortical Pyramidal Neurons in Schizophrenia. Arch. Gen. Psychiatry 57, 65; [13] Terry, R. D., Masliah, E., Salmon, D. P., Butters, N., DeTeresa, R., Hill, R., Hansen, L. A., and Katzman, R. (1991) Physical basis of cognitive alterations in Alzheimer's disease: synapse loss is the major correlate of cognitive impairment. Ann. Neurol. 30, 572-80; [14] Selkoe, D. J. (2002) Alzheimer's disease is a synaptic failure. Science 298, 789-91; [15] Walsh, D. M., and Selkoe, D. J. (2004) Deciphering the molecular basis of memory failure in Alzheimer's disease. Neuron 44, 181-93; [16] Jacobsen, J. S., Wu, C.-C., Redwine, J. M., Comery, T. A., Arias, R., Bowlby, M., Martone, R., Morrison, J. H., Pangalos, M. N., Reinhart, P. H., and Bloom, F. E. (2006) Early-onset behavioral and synaptic deficits in a mouse model of Alzheimer's disease. Proc. Natl. Acad. Sci. U.S.A 103, 5161-6; [17] Habib, L. K., Lee, M. T. C., and Yang, J. (2010) Inhibitors of catalase-amyloid interactions protect cells from beta-amyloid-induced oxidative stress and toxicity. J. Biol. Chem. 285, 38933-43; [18] Megill, A., Lee, T., Dibattista, A. M., Song, J. M., Spitzer, M. H., Rubinshtein, M., Habib, L. K., Capule, C. C., Mayer, M., Turner, R. S., Kirkwood, A., Yang, J., Pak, D. T. S., Lee, H.-K., and Hoe, H.-S. (2013) A Tetra(Ethylene Glycol) Derivative of Benzothiazole Aniline Enhances Ras-Mediated Spinogenesis. J. Neurosci. 33, 9306-9318; [19] Song, J. M., DiBattista, A. M., Sung, Y. M., Ahn, J. M., Turner, R. S., Yang, J., Pak, D. T. S., Lee, H.-K., and Hoe, H.-S. (2014) A tetra(ethylene glycol) derivative of benzothiazole aniline ameliorates dendritic spine density and cognitive function in a mouse model of Alzheimer's disease. Exp. Neurol. 252, 105-13; [20] Penzes, P., Cahill, M. E., Jones, K. A., VanLeeuwen, J.-E., and Woolfrey, K. M. (2011) Dendritic spine pathology in neuropsychiatric disorders. Nat. Neurosci. 14, 285-293; [21] Smith, D. L., Pozueta, J., Gong, B., Arancio, O., and Shelanski, M. (2009) Reversal of long-term dendritic spine alterations in Alzheimer disease models. Proc. Natl. Acad. Sci. U.S.A 106, 16877-82; [22] Selkoe, D. J. (2013) The therapeutics of alzheimer's disease where we stand and where we are heading. Ann. Neurol., 74, 328-336; [23] Prangkio, P., Rao, D. K., Lance, K. D., Rubinshtein, M., Yang, J., and Mayer, M. (2011) Self-assembled, cation-selective ion channels from an oligo (ethylene glycol) derivative of benzothiazole aniline. Biochim. Biophys. Acta 1808, 2877-85; [24] Kramer, J. A., Sagartz, J. E., and Morris, D. L. (2007) The application of discovery toxicology and pathology towards the design of safer pharmaceutical lead candidates. Nat. Rev. Drug Discov. 6, 636-49; [25] Inbar, P., Li, C. Q., Takayama, S. A., Bautista, M. R., and Yang, J. (2006) Oligo(ethylene glycol) derivatives of thioflavin T as inhibitors of protein-amyloid interactions. Chembiochem 7, 1563-6; [26] Finkelstein, H. (1910) Darstellung organischer Jodide aus den entsprechenden Bromiden and Chloriden. Berichte der Dtsch. Chem. Gesellschaft 43, 1528-1532; [27] Chittiboyina, A. G., Venkatraman, M. S., Mizuno, C. S., Desai, P. V, Patny, A., Benson, S. C., Ho, C. I., Kurtz, T. W., Pershadsingh, H. A., and Avery, M. A. (2006) Design and synthesis of the first generation of dithiolane thiazolidinedione- and phenylacetic acid-based PPARgamma agonists. J. Med. Chem. 49, 4072-84; [28] Namboodiri, V. V., and Varma, R. S. (2002) Solvent-Free Sonochemical Preparation of Ionic Liquids. Org. Lett. 4, 3161-3163; [29] Ranu, B. C., and Jana, R. (2006) Ionic Liquid as Catalyst and Reaction Medium—A Simple, Efficient and Green Procedure for Knoevenagel Condensation of Aliphatic and Aromatic Carbonyl Compounds Using a Task-Specific Basic Ionic Liquid. European J. Org. Chem. 2006, 3767-3770; [30] Schaumann, E. (ed.) (2007) Sulfur-Mediated Rearrangements I, Springer Berlin Heidelberg, Berlin, Heidelberg; [31] Yang, J., Gabriele, B., Belvedere, S., Huang, Y., and Breslow, R. (2002) Catalytic Oxidations of Steroid Substrates by Artificial Cytochrome P-450 Enzymes †. J. Org. Chem. 67, 5057-5067; [32] Datki, Z., Juhász, A., Gálfi, M., Soós, K., Papp, R., Zádori, D., and Penke, B. (2003) Method for measuring neurotoxicity of aggregating polypeptides with the MTT assay on differentiated neuroblastoma cells. Brain Res. Bull. 62, 223-229; [33] Djakovic, S. N., Schwarz, L. A., Barylko, B., DeMartino, G. N., and Patrick, G. N. (2009) Regulation of the proteasome by neuronal activity and calcium/calmodulin-dependent protein kinase II. J. Biol. Chem. 284, 26655-65; [34] Cartier, A. E., Djakovic, S. N., Salehi, A., Wilson, S. M., Masliah, E., and Patrick, G. N. (2009) Regulation of synaptic structure by ubiquitin C-terminal hydrolase L1. J. Neurosci. 29, 7857-68; [35] Furuta, T., Tomioka, R., Taki, K., Nakamura, K., Tamamaki, N., and Kaneko, T. (2001) In vivo transduction of central neurons using recombinant Sindbis virus: Golgi-like labeling of dendrites and axons with membrane-targeted fluorescent proteins. J. Histochem. Cytochem. 49, 1497-508; [36] Zhao, X., and Yang, J. (2010) Amyloid-β peptide is a substrate of the human 20S proteasome. ACS Chem. Neurosci. 1, 655-660; [37] Krapivinsky, G., Krapivinsky, L., Manasian, Y., Ivanov, A., Tyzio, R., Pellegrino, C., Ben-Ari, Y., Clapham, D. E., and Medina, I. (2003) The NMDA Receptor Is Coupled to the ERK Pathway by a Direct Interaction between NR2B and RasGRF1. Neuron 40, 775-784; [38] DMSO was used for all compounds due to its necessity to solubilize BTA-EG4; [39] Prangkio, P., Yusko, E. C., Sept, D., Yang, J., and Mayer, M. (2012) Multivariate analyses of amyloid-beta oligomer populations indicate a connection between pore formation and cytotoxicity. PLoS One 7, e47261; [40] Murphy, D. D., and Segal, M. (1996) Regulation of Dendritic Spine Density in Cultured Rat Hippocampal Neurons by Steroid Hormones. J. Neurosci. 16, 4059-4068; [41] Peters, A., and Kaiserman-Abramof, I. R. (1970) The small pyramidal neuron of the rat cerebral cortex. The perikaryon, dendrites and spines. Am. J. Anat. 127, 321-355; [42] Serrano-Pozo, A., Frosch, M. P., Masliah, E., and Hyman, B. T. (2011) Neuropathological alterations in Alzheimer disease. Cold Spring Harb. Perspect. Med. 1, a006189.

What is claimed is:

1. A compound having the formula (I):

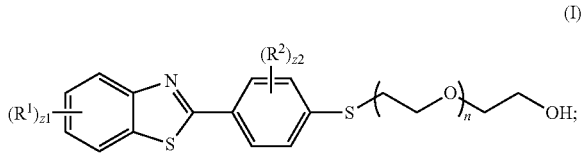

wherein

R¹ is independently
halogen, —CX¹₃, —CHX¹₂, —CH₂X¹, —OCX¹₃, —OCHX¹₂, —OCH₂X¹, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, NHC(O)NH₂, —NHSO₂H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is independently
halogen, —CX²₃, —CHX²₂, —CH₂X², —OCX²₃, —OCHX²₂, —OCH₂X², —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X¹ and X² are independently halogen;

z1 and z2 are independently an integer from 0 to 4; and n is an integer from 1 to 12.

2. The compound of claim 1, wherein R¹ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

3. The compound of claim 1, wherein R¹ is substituted or unsubstituted alkyl.

4. The compound of claim 1, wherein R² is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

5. The compound of claim 1, wherein R² is substituted or unsubstituted alkyl.

6. The compound of claim 1, wherein z1 is 0 or 1.

7. The compound of claim 1, wherein z1 is 0.

8. The compound of claim 1, wherein z2 is 0.

9. The compound of claim 1, wherein n is 3 to 8.

10. The compound of claim 1, wherein n is 3 to 5.

11. The compound of claim 1, having the formula:

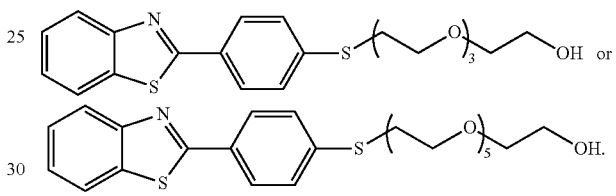

12. A pharmaceutical composition comprising a pharmaceutically acceptable excipient and a compound of claim 1.